(12) United States Patent
Osorio

(10) Patent No.: US 10,226,220 B2
(45) Date of Patent: *Mar. 12, 2019

(54) DETECTING, ASSESSING AND MANAGING A RISK OF DEATH IN EPILEPSY

(71) Applicant: Ivan Osorio, Leawood, KS (US)

(72) Inventor: Ivan Osorio, Leawood, KS (US)

(73) Assignee: FLINT HILLS SCENTIFIC, LLC, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/796,887

(22) Filed: Oct. 30, 2017

(65) Prior Publication Data

US 2018/0049704 A1    Feb. 22, 2018

Related U.S. Application Data

(63) Continuation of application No. 15/333,802, filed on Oct. 25, 2016, now Pat. No. 9,808,207, which is a (Continued)

(51) Int. Cl.
*A61B 5/00* (2006.01)
*A61N 1/365* (2006.01)
(Continued)

(52) U.S. Cl.
CPC .............. *A61B 5/746* (2013.01); *A61B 5/021* (2013.01); *A61B 5/0205* (2013.01);
(Continued)

(58) Field of Classification Search
None
See application file for complete search history.

(56) References Cited

U.S. PATENT DOCUMENTS 8,562,524 B2 * 10/2013 Osorio ................. A61B 5/7275
600/300
9,504,390 B2 * 11/2016 Osorio ................. A61B 5/0205
(Continued)

*Primary Examiner* — Brian T Gedeon
(74) *Attorney, Agent, or Firm* — CF3; Stephen Eisenmann

(57) ABSTRACT

A method for determining and responding in real-time to an increased risk of death relating to a patient with epilepsy is provided. The method includes receiving cardiac data and determining a cardiac index based upon the cardiac data. The method includes determining an increased risk of death associated with epilepsy if the indices are extreme, issuing a warning of the increased risk of death and logging information related to the increased risk of death. Also presented is a second method for determining and responding in real-time to an increased risk of death relating to a patient with epilepsy comprising receiving at least one of arousal data, responsiveness data or awareness data and determining an arousal index, a responsiveness index or an awareness index, where the indices are based on arousal data, responsiveness data or awareness data respectively. The second method includes determining an increased risk of death related to epilepsy if indices are extreme values, issuing a warning of the increased risk of death and logging information related to the increased risk of death. A computer readable program storage device is also provided. Also provided is a method for receiving body data, determining a cardiac, an arousal, a responsiveness, or a kinetic index, determining an increased or increasing risk of death over a first time window relating to a patient with epilepsy and issuing a warning and logging relevant information.

24 Claims, 17 Drawing Sheets

Related U.S. Application Data continuation of application No. 14/026,998, filed on Sep. 13, 2013, now Pat. No. 9,504,390, which is a continuation of application No. 13/091,033, filed on Apr. 20, 2011, now Pat. No. 8,562,524, which is a continuation-in-part of application No. 13/040,996, filed on Mar. 4, 2011, now Pat. No. 8,562,523.

(51) Int. Cl.
| | |
|---|---|
| *A61B 5/0205* | (2006.01) |
| *A61B 5/08* | (2006.01) |
| *A61B 5/021* | (2006.01) |
| *A61B 5/0245* | (2006.01) |
| *A61B 5/11* | (2006.01) |
| *A61N 1/39* | (2006.01) |
| *A61N 1/36* | (2006.01) |
| *A61B 5/0452* | (2006.01) |
| *A61B 5/16* | (2006.01) |
| *A61F 7/00* | (2006.01) |
| *A61M 5/172* | (2006.01) |
| *G16H 50/30* | (2018.01) |
| *G06F 19/00* | (2018.01) |
| *A61N 1/372* | (2006.01) |

(52) U.S. Cl.
CPC ........ *A61B 5/02455* (2013.01); *A61B 5/0452* (2013.01); *A61B 5/0826* (2013.01); *A61B 5/1118* (2013.01); *A61B 5/162* (2013.01); *A61B 5/4094* (2013.01); *A61B 5/7275* (2013.01); *A61F 7/00* (2013.01); *A61M 5/1723* (2013.01); *A61N 1/36064* (2013.01); *A61N 1/36139* (2013.01); *A61N 1/36514* (2013.01); *A61N 1/36585* (2013.01); *A61N 1/3987* (2013.01); *G06F 19/00* (2013.01); *G16H 50/30* (2018.01); *A61B 5/02055* (2013.01); *A61B 5/4836* (2013.01); *A61B 5/4839* (2013.01); *A61M 2230/06* (2013.01); *A61M 2230/20* (2013.01); *A61M 2230/201* (2013.01); *A61M 2230/208* (2013.01); *A61M 2230/30* (2013.01); *A61M 2230/42* (2013.01); *A61M 2230/63* (2013.01); *A61N 1/36142* (2013.01); *A61N 1/37247* (2013.01); *A61N 1/37258* (2013.01)

(56) References Cited

U.S. PATENT DOCUMENTS 9,808,207 B2 * 11/2017 Osorio ................ A61B 5/0205
2011/0306845 A1 * 12/2011 Osorio ................ G16H 15/00
600/300

* cited by examiner

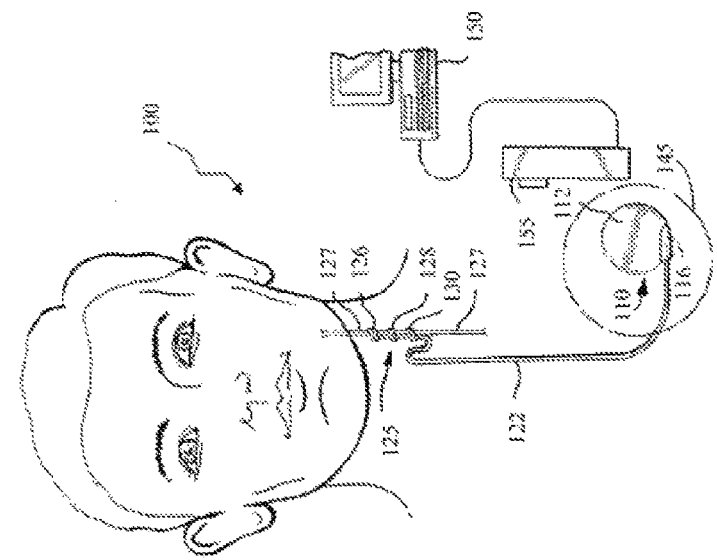
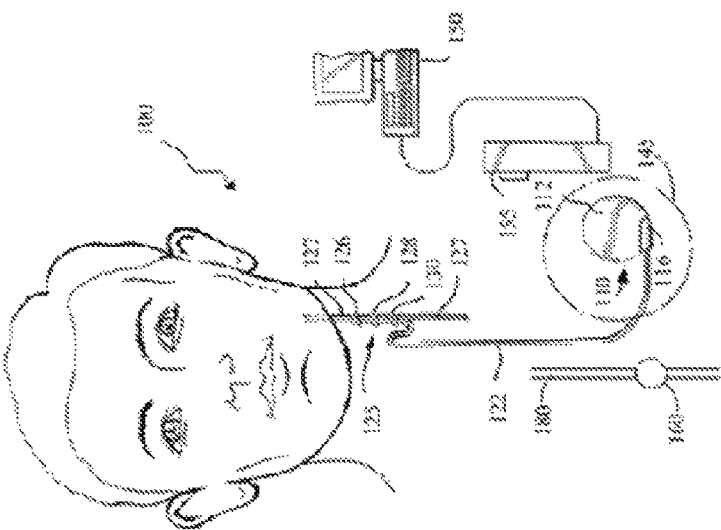
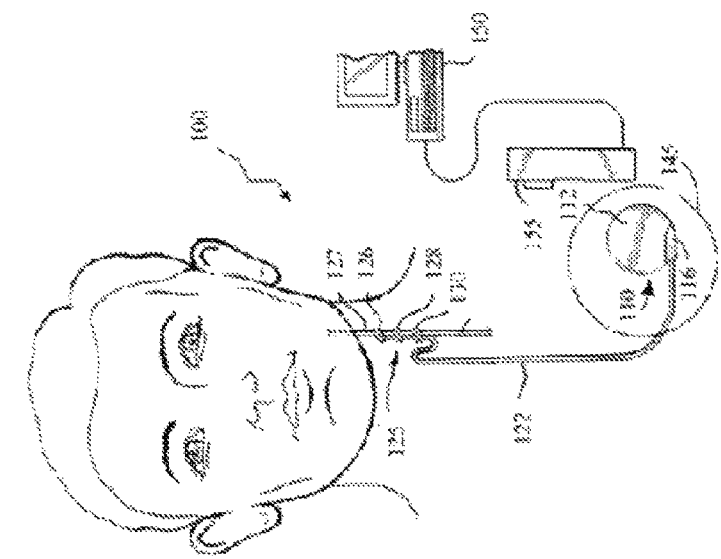

DETECTING, ASSESSING AND MANAGING A RISK OF DEATH IN EPILEPSY

CROSS-REFERENCE TO RELATED APPLICATIONS

The present application is a Continuation of U.S. patent application Ser. No. 15/333,802, filed on Oct. 25, 2016; which is a Continuation of U.S. patent application Ser. No. 14/026,998, filed on Sep. 13, 2013; which is a Continuation of U.S. patent application Ser. No. 13/091,033, filed on Apr. 20, 2011; which is Continuation-in-Part of U.S. Ser. No. 13/040,996, filed on Mar. 4, 2011. Each of these U.S. patent application Ser. Nos. 15/333,802, 14/026,998, 13/091,033, and 13/040,996 are hereby incorporated by reference in their entirety.

BACKGROUND

1. Field of the Invention

This invention relates generally to medical device systems and, more particularly, to medical device systems and methods capable of estimating the risk of death (an extreme event) at various time-scales and managing said risk in a patient with seizures and epilepsy.

2. Description of the Related Art

Standardized mortality rates in epilepsy patients are higher than in the general population by two to threefold. Relative survivorship (RS) following the diagnosis of epilepsy decreases as the time from diagnosis increases (91% after 5 years; 85% after 10 years; 83% after 15 years. In patients with frequent and severe seizures (pharmaco-resistant epilepsy) mortality is much higher than in those with infrequent seizures, with standardized mortality ratios ranging from 2.2-6.5. Even higher mortality is found in patients with epilepsy and congenital or peri-natal neurological deficits with standardized mortality ratios between 7 and 50.

The various teachings herein conflate new knowledge into embodiments to fill the technology void for prevention of premature death and the crippling neurological sequelae due to late intervention, while addressing the limitations of the existing art which has little if any clinical value. For example, unlike U.S. PUB 2010/0198289, embodiments described herein estimate the risk of death not just of SUPED which although the most dramatic form, accounts for less than $\frac{1}{5}^{th}$ of all epilepsy related deaths. This application addresses said limitations of the art, using a multi-variate (autonomic, neurologic, metabolic signals, etc.) approach at multiple time scales using past behavior (system's history) not just univariately (breathing), at one time scale taking that takes into consideration only one event in the present as U.S. PUB 2010/019828. The embodiments herein incorporate not just rate but also rhythm, pattern and morphology of not just respiratory but also of cardiac and other autonomic activity and neurologic activity which increase predictive power of risk of death; the embodiments herein take into account multiple state factors, the environment and the condition of the patient which may increase risk death, unlike US PUB 2010/0198289 which limits the search to seizures; the embodiments herein use seizure severity, inter-seizures interval, site of seizure origin, etc.; the embodiments herein test arousal and responsiveness which not only increases sensitivity and specificity of risk of death estimates but does not ignore (for performance optimization) that death in epilepsy is not restricted to sleep and in over 80% is not unexplained; the embodiments herein exploit the "built-in" protection against cardiac or respiratory depression/arrest afforded by increased levels of reticulo-thalamo-cortical reticular activation by upwardly modulating them when necessary. At a more fundamental level, the practice of U.S. PUB 2010/0198289 exhibits further deficiencies. 1. Unlike the embodiments herein, it has no power to discriminate within a clinically useful/safe time, apneas and hypopneas occurring in the context of obstructive (or central) sleep apnea syndrome from those of SUDEP. This will result in potentially tens/hundreds of false positive detections each night, rendering that approach useless (patients and caregivers will reject any method that issues multiple nightly false warning of impending death). Given the embodiments of that application (all univariate and without regard for the system's history) the only way to decrease the intolerable (to patients and caregivers) large number of false positives is to increase the SUDEP index threshold to such a high level that the risk will not be identified, if at all, until it will be too late for prevention of death or of hypoxic-ischemic brain damage. Specifically, U.S. PUB 2010/0198289, unlike the instant disclosure, cannot accurately distinguish (until it is too late) apneas of SUDEP or of death from those associated with sleep apnea syndromes; 2. Its treatment of seizures is likely to increase, not decrease the risk of death because: a) "vagal nerve stimulation modifies synchronization between cardiac and respiratory activity, resulting in poor optimization of oxygen delivery to tissues that can be regarded as an additive side effect, which should be considered in patients with already altered brain function. This interaction between the effects of VNS and potential autonomic nervous system dysfunction already reported in epileptic patients should be considered to be potentially life-threatening" (Epilepsia 2009; 50(11): 2473-80); b) it increases the resistance of the upper airways to the passage of air (Epilepsy Res. 010; 89(2-3):227-31) and causes bronchial hyperreactivity and increase in secretions, both of which reduce gas exchange (Bull Eur Physiopathol Respir. 1986; 22 Suppl. 7:112-42).

Sleep apnea syndromes which are more prevalent than epilepsy manifest with hypopneas and apneas that recur aperiodically and frequently (tens to hundreds of events each night). Estimating the risk of SUDEP in patients with epilepsy and these syndromes is fraught with uncertainty and thus of little clinical value if this estimation is based only on a short monitoring window (one event at a time) and only one biologic signal (respirations). The embodiments herein overcome these serious limitations by using windows of various lengths (10 s to months) and incorporating into the estimate of risk of death, features such as apnea duration, magnitude, frequency, inter-apnea intervals as a function of sleep cycle, treatment with CNS depressant drugs (that blunt alertness), fitness level and health status of a patient among others. By characterizing (over days to weeks) these variables and building for example probability density functions, it is then and only then, possible to issue useful estimates of the risk of SUDEP.

This is the first invention to utilize not only neurologic, autonomic and other body signals but do so at informative and therapeutically useful time scales, in a multi-variate adaptive manner to optimize sensitivity and specificity of detection of factors correlated with or causative of death in epilepsy and to institute therapies that prevent a fatal outcome as well as irreversible damage to body organs.

SUMMARY OF EMBODIMENTS

In one aspect of the present invention, a method for determining and responding in real-time to an increased risk of death relating to a patient with epilepsy is provided. The method includes receiving cardiac data into a medical device and determining, using the medical device, at least one cardiac index, the at least one cardiac index being based upon the cardiac data. The method also includes determining, using the medical device, an increased risk of death associated with epilepsy if the at least one cardiac index is an extreme value, issuing automatically a warning of the occurrence of the increased risk of death and logging automatically information related to the increased risk of death.

In another aspect of the present invention, a method for determining and responding in real-time to an increased risk of death relating to a patient with epilepsy is provided. The method includes receiving at least one of arousal data, responsiveness data or awareness data into a medical device and determining, at the medical device, at least one of an arousal index, a responsiveness index or an awareness index, the at least one of an arousal index, a responsive index or an awareness index being based upon the arousal data, responsiveness data or the awareness data respectively. The method also includes determining, at the medical device, an increased risk of death related to epilepsy if the at least one of an arousal index, a responsiveness index or an awareness index is an extreme value, issuing automatically a warning of the occurrence of the increased risk of death and logging automatically information related to the increased risk of death.

In yet another aspect of the present invention, a non-transitory, computer-readable storage device for storing instructions that, when executed by a processor, perform a method for determining in real-time of an increased risk of death relating to a patient with epilepsy, is presented. The method includes receiving at least one of cardiac data, arousal data or responsiveness data into a processing device and determining at least one of a cardiac index or an arousal index or a responsiveness index, the at least one of a cardiac index, an arousal index or a responsiveness index being based upon cardiac data or arousal data or responsiveness data respectively. Also included is determining an increased risk of death associated with epilepsy if at least one of the cardiac index, the arousal index or the responsiveness index is an extreme value, issuing automatically a warning of the occurrence of the increased risk of death and logging automatically information related to the increased risk of death.

In yet another aspect of the present invention, a method is provided for receiving body data into a medical device, determining, at the medical device, at least one of a cardiac index, an arousal index, a responsiveness index, or a kinetic index based at least upon the body data and determining, at the medical device, at least one of an increased risk of death or an increasing risk of death over a first time window relating to a patient with epilepsy based at least upon the at least one determined index. The increased risk of death relating to epilepsy and the increasing risk of death relating to epilepsy comprise at least one of a seizure coupled with at least one of bradycardia or asystole or a lack of arousability or of responsiveness of the patient, at least one patient condition, patient activity or environmental circumstance external to the seizure event that when coupled with a seizure cause an increased or increasing risk of death, or a seizure that has a higher than normal risk of death. The method also includes issuing automatically a warning in real-time of the occurrence of the identified increased risk of death or increasing risk of death over a first time window to at least one of the patient, a caregiver or emergency response personnel and logging automatically relevant information related to the identified increased risk of death or increasing risk of death over a first time window.

BRIEF DESCRIPTION OF THE DRAWINGS

The invention may be understood by reference to the following description taken in conjunction with the accompanying drawings, in which like reference numerals identify like elements, and in which:

FIG. 1A provides a stylized diagram of a medical device which may be implanted into a patient's body for providing a therapeutic electrical signal to a body organ, in accordance with one illustrative embodiment of the present invention;

FIG. 1B provides a stylized diagram of a medical device which may be implanted into a patient's body for providing a therapeutic electrical signal to a neural structure of the patient's body, in accordance with one illustrative embodiment of the present invention;

FIG. 1C provides a stylized diagram of a medical device which may be implanted into a patient's body for providing a therapeutic electrical signal to a neural structure of the patient's body, in accordance with one illustrative embodiment of the present invention;

Figure 1D:
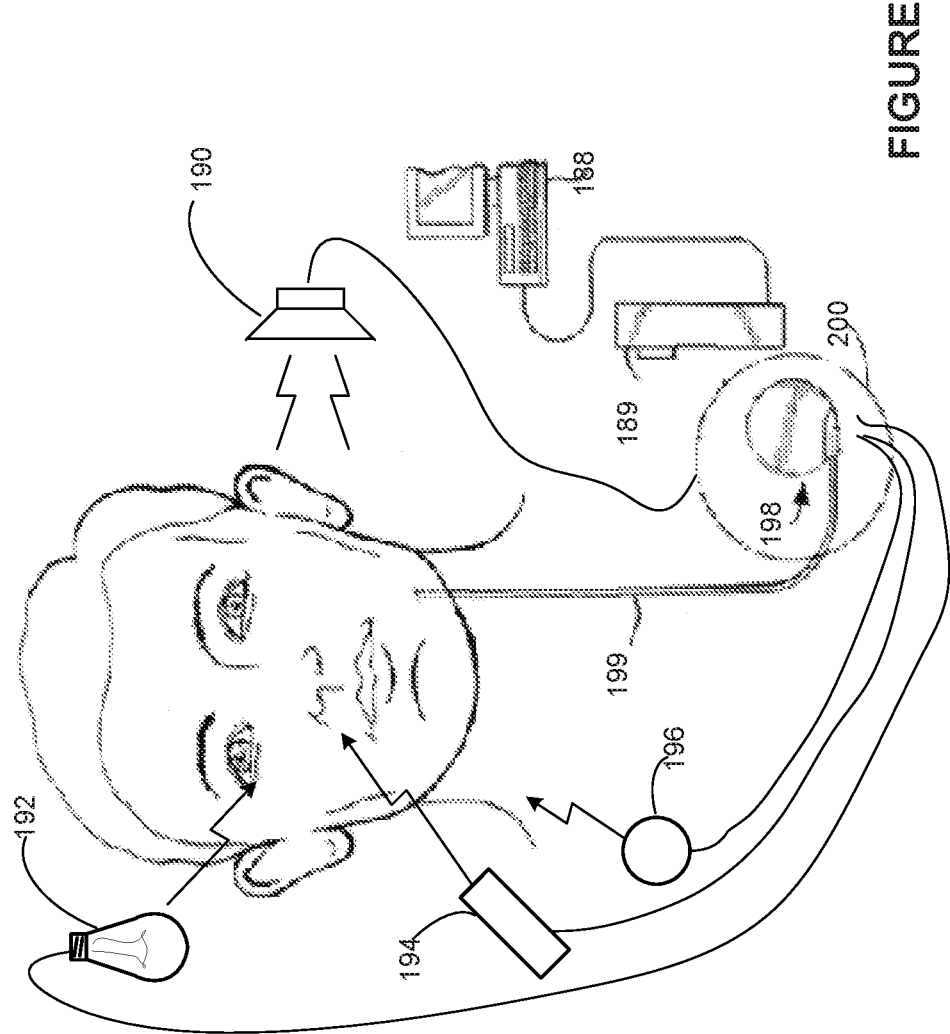
FIG. 1D provides a stylized diagram of a medical device which may or may not be implanted into a patient's body for providing one or more stimuli to the patient, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated. The terms "adapted to" and "capable of" as used herein may imply, among other things, that a device has a structure sufficient to perform some task or operation. The terms "adapted to" and "capable of" are not used to state (implicitly or explicitly) mere intended use limitations in the description and claims of the instant Application.

The term "electrode" or "electrodes" described herein may refer to one or more stimulation electrodes (i.e., electrodes for delivering a therapeutic signal generated by an MD to a tissue), sensing electrodes (i.e., electrodes for sensing a physiological indication of a patient's body), and/or electrodes that are capable of delivering a therapeutic signal, as well as performing a sensing function.

The terms "ictal" and "seizure" as described herein, may be used interchangeably to mean the period of time during an epileptic cycle in which seizures occur. An epileptic cycle may be divided into three sub-cycles: ictal/seizure (e.g., partial, complex-partial, simple-partial seizure events), post-ictal (e.g., a time period after the ictal period, but before the patient returns to the inter-ictal or baseline levels of function) and inter-ictal when the patient's body functions are at a baseline or "normal" level for the patient Epileptic seizure events may refer to any adverse events (whether extreme or non-extreme) occurring in an epileptic patient that are: a) directly, or indirectly related to the occurrence of seizures; b) directly unrelated to the occurrence of seizures and as such may occur in the post-ictal or inter-ictal periods.

The term, and concept of, "responsiveness" as used in reference to the embodiments described herein, has a motor and a cognitive component which may be strongly correlated or dissociated; further the motor component may be in the form of a simple response (e.g., withdrawal of a limb from a pain source) or complex (e.g. drawing a triangle in response to a command). Consequently, responsiveness may be tested using simple stimuli (e.g., acoustic in the form of a loud noise or sensory in the form of a pinprick) or complex (e.g., complex reaction time tests; questions probing knowledge, judgment, abstraction, memory, etc.). In this invention, when "responsiveness" is tested using complex stimuli, "awareness" is being probed and therefore in that case these terms/concepts are used interchangeably. The meaning of "responsiveness" is thus, context dependent: if the objective is to determine if a patient generates simple motor responses or movements, the term "responsiveness" may be used and if it is to test the presence and quality of complex responses, "awareness" may replace responsiveness. Responsiveness and awareness are critically dependent, for normal function, on the integrity of: a) the reticular activating system; b) motor sensory, visual, hearing, among other functions. The reticular activating system plays a key role in arousability as it determines a patient's susceptibility to being awakened from a physiologic (e.g., sleep) or pathologic (e.g., post-ictal state associated with a generalized tonic-clonic seizure) state. Arousability may be defined herein as increases in EMG activity insufficient in extent and intensity to cause joint movements or increases in heart rate, respiratory rate or blood pressure in close temporal proximity to the presentation of a stimulus. In one embodiment of this invention, the risk of death will be estimated by sequentially assessing arousability, simple responsiveness and complex responsiveness or awareness. The degree of a patient's arousability must be taken into account when assessing risk of death: Epileptic patients who are not arousable (e.g., comatose) are at a higher risk of death than those who are arousable and patients who are arousable and capable of generating only simple motor responses are in turn at higher risk of death that those who are not only capable of simple but also of complex responses and considered as being "aware". In another embodiment, simple or complex responsiveness may be tested directly without having first tested arousability; if the patient fails to take the responsiveness test, arousability may then be tested. Arousability may be measured using EMG, kinetic and autonomic indices to yield an arousability index. Arousal may be associated with, an increase in EMG activity, in heart rate, in respiratory rate, in blood pressure, in a decrease in pupillary size and/or a decrease in skin resistance. It should be noted that this list is not exclusive and may include one or more measures as would be apparent to one of ordinary skill in the art having the benefit of this disclosure. These changes are quantifiable and may be used as an index of arousability: for example, the greater the change in values, the greater the index and the more intense the arousal.

The terms "specific care" described herein refers to therapies aimed at controlling undesirable or abnormal events (e.g., defibrillation in the case of ventricular fibrillation). The term "supportive care" described herein may be care provided to a patient that is care targeted to other patient needs such as breathing (oxygen), body and/or brain cooling, non-seizure medications and/or drugs, fluid intake, intubation, and/or the like.

The terms "mesoscopic," "microscopic" and "macroscopic" described herein denoted time periods for observation and quantification of body organs/systems indices during ictal, post-ictal or inter-ictal periods for the purpose of determining if they are extreme and this associated with further increases in the risk of death Said indices included but are not limited to heart rate, P-QRS-T complex morphology and intervals, heart rate variability, respiratory rate and pattern, blood pressure and/or other body data described herein. "Microscopic" may correspond to a scale of observation of up to 4 minutes (the window during which brain function is not irreversibly affected by hypoxia or ischemia) "Mesoscopic" may correspond to a scale of observation between 4 minutes and 24 hours); this scale allows identification of trends in certain indices arousability, responsiveness and/or awareness. "Macroscopic" may correspond to an scale of observation longer than 24 hours that may be used to detect changes that occur at a slow rate (weeks to years) and determine whether or not they are reversible and if not their rate of progression. Cognitive functions, state of the epileptic disorder and/or of the patient's general health and certain cardiac function indices such as heart rate variability are among those best suited for evaluation at this scale. In the context of the description provided herein, the term "window" may be used to refer to one or more of the "microscopic" "mesoscopic," and "macroscopic" time periods described above.

The concept of time scales (e.g., "microscopic" "mesoscopic," and "macroscopic" may be also used to classify the risk of death as: a) sudden/imminent if the change in an index lasting up to four minutes may have serious or fatal consequences (e.g., asystole or apnea); b) as potentially predictable if the serious or fatal changes develop gradually (over several minutes to 24 hours) or hours thus providing a longer time window for treatment than those operating over a microscopic scale (e.g., pulmonary edema); or c) increased but temporally remote if the scale is macroscopic (e.g., first recorded change in heart rate variability (HRV)). Risk of death in epileptic patients is multi-factorial and may be independent of the intensity, duration extent of spread or inter-seizure interval and frequency. An epilepsy patient's: 1. Activity (e.g., swimming, climbing a ladder, operating a motor vehicle or power equipment); 2. Condition (e.g., healthy and physical fit vs. ill) including mental health and emotional state; and 3. Environment (e.g., working in a kitchen as a cook) may be important determinants of risks of death or injury and may be taken into account for estimation purposes.

Depending on the underlying causes, autopsy findings (or lack thereof) and the probability of occurrence based on factors such as age, occupation and state of health among other factors, death may be classified as: a) sudden unexpected and un-explained (SUDEP) as in the case of a patient with pharmaco-resistant seizures, otherwise healthy who collapses to the floor dead in front of witnesses with the autopsy providing no clues as to cause of death; b) unexpected but explainable as in the case of a patient with well-controlled epilepsy patient who is found dead in bath tub filled with water; the autopsy confirms drowning as the cause of death and further that were no traces of the prescribed anti-seizure drugs in body fluids making a seizure the most likely primary cause of death; c) neither sudden, nor un-expected, nor un-explained as in the case of a patient with pharmaco-resistant seizures who goes into status epilepticus, which cannot be controlled and dies several days later in an ICU due multiple organ failure.

Sudden, unexpected, unexplained death (SUDEP) is the most perplexing, accounting for 8-17% of all deaths in patients with epilepsy. In adolescents and young adults, SUDEP is 24-40 times more common than in the general population, The risk factors for SUDEP are classified into: 1. Patient Risk Factors: a) Age (25-35 year-old are most vulnerable); b) Gender (Males succumb at a ratio of 7:4; c) Race (African-Americans are at highest risk); d) Neurologic deficits particular if congenital/perinatal and severe); e) Having a mutation in a gene called Kv1.1; f) Excessive alcohol consumption; 2, Seizure Risk Factors: a) Symptomatic epilepsy; b) Generalized Tonic-Clonic; c) Onset at early age; d) Having epilepsy for over ten years; e) Having a high number of seizures; f) History of status epilepticus; g) Having had seizures shortly before death; h) Not being in remission and off medication for at least 5 years; 3. Treatment Risk Factors: a) Recent change in treatment; b) Sub-therapeutic concentrations of anti-seizure drugs; c) Taking multiple anti-seizure drugs; d) History of epilepsy surgery; e) High serum concentration of carbamazepine.

In various embodiments of this invention, death whether sudden or not sudden, unexpected or unexplained may be considered (and managed) as an extreme event along with its associated risks. Other common examples of extreme events (that carry also increase the risk of death) are generalized or partial status epilepticus.

A patient may have certain kinds of seizures which may be classified as "non-extreme" and "extreme", both of which may increase the risk of death or of SUDEP via different mechanisms. As defined herein, "extreme" seizures are classified based on certain metrics such as a seizure intensity, duration or extent of spread, inter-seizure interval duration and/or the impact the extreme seizures have on a subject (which may be dependent or independent of intensity, duration, extent of spread or inter-seizure interval duration), also called the patient seizure impact (PSimp). Extreme events may be defined quantitatively or qualitatively. Quantitatively, as defined herein, they correspond for example to those to the far right (on the x-axis) of a probability density function, or in the case of a normal/normalized distribution to those more than two standard deviations beyond the mean or as above (e.g., $80^{th}$) or below ($20^{th}$) percentile of a distribution, or also as those whose conditional probability of occurrence is very low, yet they "defy the odds" in a statistical sense, (e.g., unexpected). Qualitatively, extreme events as defined herein, are those whose severity (e.g. intensity, duration, etc.), frequency or impact on body organs/systems (reversible or irreversible) among others, exceeds (in magnitude or type) expected and commonly observed outcomes. For example. A patient with long history of convulsions, develops pulmonary edema after one of these seizures. The fact that its impact (pulmonary edema) is both serious and rare/unprecedented makes this seizure "extreme". It should be noticed that for an epileptic event to qualify as extreme it need only be severe or rare.

As for the patient impact, a seizure may be considered extreme (regardless of energy, severity or inter-seizure interval measures, if it is causes: system dysfunction of a type, magnitude, duration and/or frequency (number of dysfunctions/unit time) exceeding the ictal or post-ictal baseline dysfunction for that subject, or if the seizure causes the subject to sustain injuries. The seizure impact on a patient may be captured with two measures: 1. Patient Seizure Impact (PSimp), which takes into account adverse effects in organ/systems associated with, or attributable to, a seizure, and which are short-lived (e.g., minutes) and are fully reversible; and 2. Patient Seizure Burden (PSB) which takes into account: i) adverse effects on organs/systems which are either reversible but longed lived (e.g., bone fracture caused a tonic-clonic seizure) or irreversible (brain damage caused by hypoxia during a prolonged tonic seizure); and ii) Quality of Life (QOL). In one or more embodiments, PSimp and/or PSB may reflect SSI and ISI values, while in other embodiments, PSimp and/or PSB may not reflect SSI and ISI values. PSimp may be determined qualitatively or quantitatively using any index from any organ/system in any possible number or combinations. For example, the most recent seizure was associated with transient S-T segment elevation (qualitative) or the most recent seizure was associated with S-T segment elevation of 1 mm which lasted for 30 minutes (quantitative). In the embodiments described herein, PSimp may be determined for each seizure and may not take into account the cumulative impact of previous seizures e.g., over a certain time window, while seizure burden, may a cumulative or longitudinal measure used in this invention, takes into account previous seizures. It should be noted that the inherent/baseline or increased increase risk of death with seizures may be sensitively dependent on conditions and/or circumstances and type of activity in which the patient is engaged at the time of a seizure.

The concept of "extreme" may take different meanings for different fields. Extreme value theory (EVT) in math is a specific corpus in which limit theorems have been developed that are similar to the central limit theorem for the sum of random variables, but here for the extreme of maximum value of a set of N variables. Such EVT theorems apply to any distribution, power law or not. When the N random variables are independent, the theorem states that the distribution of the maximum among these N variables (the "extreme") can only be one of three types: Frechet (power law tail), Gumbel (exponential type) and Weibull (upper bound and exponential of power law on the other side). However, EVT theorems may not encompass all possible permutations because there are "dragon-kings" beyond these extremes, resulting from special amplification (like global synchronization), which is not accounted for by the probability density function of the rest of the distribution (See D. Sornette. Dragon-Kings, Black Swans and the Prediction of Crises, International Journal of Terraspace Science and Engineering 2009; 2:1-18).

Brain activity (e.g., electrical, cognitive, affective), whether normal or abnormal (e.g., seizures), may affect the function of the autonomic nervous system. Moreover, given the close interaction between the autonomic nervous system and organs to which it is coupled (e.g., heart, lungs, pupils), these organs may also be profoundly affected by brain activity. Examples of the effects of brain activity include changes in respiratory rates and heart rhythms. More specifically, one striking example of the interaction between brain state and the cardio-respiratory system is the observation that anesthetized humans breathing spontaneously, stopped breathing at reduced arterial concentrations of $CO_2$ that did not impair/alter their breathing while awake. This phenomenon known as the "wakefulness effect" underscores: a) the vital importance of the activating role on cardio-respiratory functions of increased neural influences present during wakefulness compared to depressed levels of consciousness, as seen for example during certain seizures or immediately after their termination; placed in a clinical/practical context, a reticulo-thalamo-cortical system that is either activated or can be activated, is a safeguard against extreme or catastrophic events of a cardio-respiratory nature; b) the greater susceptibility to respiratory and cardiac dysfunction in subjects with depressed levels of consciousness whether physiologic (e.g., sleep) or pathologic (ictal or post-ictal states); said dysfunction is not limited to changes in rate or tidal volume (e.g. hypopnea, apnea or hypoventilation) but encompass rhythm (cardiac or respiratory arrhythmias), pattern (e.g. Cheyne-Stokes breathing; agonal breathing) or morphology of either EKG complexes (e.g. PVC's, S-T segment elevation) or breaths (e.g., apneustic breathing); c) the critical importance for sensitivity, specificity and speed of detection and quantification/estimation of increased risk of death in epilepsy patients, to include tests of arousability or responsiveness in the assessment and decision, since loss of consciousness occurs within seconds of severe hypoxemia or ischemia associated with life-threatening cardio-respiratory dysfunction; it thus follows that if a patient is arousable and/or more particularly if the cognitive performance is intact the probability that the change in cardio-respiratory function is life threatening is small, if not negligible; d) the therapeutic value of delivering stimuli that cause arousal to decrease the risk of death in certain situations; this therapeutic value is inherent to or inextricable linked to the act of delivery a stimulus to test level of responsiveness; in this invention, testing is the therapy and therapy is testing.

Seizure metrics may be derived from at least one of intensity, duration spread or an inter-seizure interval (defined as the time (in seconds or minutes) elapsed between the onset of consecutive seizures; (See Osorio et al., Epilepsia 1998; 2002; EJN, 2009; PRE 2010), or from two or more in any possible combination. For example, a) a seizure severity index may be the average of the percentiles of intensity, duration and extent of spread; b) peak seizure energy may be the product of peak intensity and duration; c) the sum of seizure severity (as defined immediately above) measured at each body organ where the seizure exerts its action, divided by the total number of body organs, or more restrictively, the measurement may be limited to one organ such as brain where its severity is the sum at each brain site engaged in seizure activity; d) As the time spent in seizure over a certain time window; e) as the product of the sum of seizure severities and time spent in seizure over a certain time window. Those of ordinary skill in the art appreciate that seizure metrics may be derived using other mathematical approached. Values of seizure metrics indicative of an extreme seizure may be more than two standard deviations above the mean for seizure energy or severity and below the mean for inter-seizure intervals with respect to normal or normalized distribution. Additionally, because a seizure may impact (mildly or severely, reversibly or irreversibly) impact body organs/systems, indices may be estimated or measured for each of the following: autonomic, neurologic, tissue stress, endocrine, metabolic and/or physical fitness/integrity. For example, generalized tonic-clonic seizures (i.e., convulsion) cause transient hypoxemia, hypercarbia, tachycardia, lactic acidosis and increases in CK, among others.

As stated above, a seizure may be classified as extreme independent of its intensity, duration or extent of spread. A complex partial seizure associated with confusion and unawareness that occurs when a patient is operating a motor vehicle and leads to a collision that causes body trauma is considered extreme, while a seizure identical in type and severity when the patient is sitting at home watching TV, is not extreme as its impact on the patient is much smaller. A fall caused by a seizure that results in a skull fracture with brain hemorrhage, or fracture of some other bone is deemed extreme, regardless of its inherent severity. As such, risk of death may correlated with seizure impact qualitatively (type of impact: head trauma vs. arm trauma) and quantitatively (for head trauma, small frontal hematoma vs. large). The force of the body/head impact, a determinant of severity, is, among other factors, a function of the velocity of the falling object, the height from where the object falls, the kinetic energy before the impact and the distance the object travels after the impact. In the case of falls, the surface over which the patient falls, (concrete vs. carpet) plays a role in force of impact. Quantification of the force of impact may be performed in the embodiments herein using equations and devices known to those of ordinary skill in the art. These data may be used to estimate risk (minor or major, etc.) and/or issue appropriate, timely interventions.

A patient may have other certain kinds of seizure events which may be classified as "extreme." Seizure events such as status epilepticus, risk thereof, or increased risk thereof), risk of death, risk of SUDEP, seizure events of certain energy, severity and/or occurring within certain time intervals, seizures with certain effects (e.g., falls, cardiac and/or respiratory dysfunction, cardiac and/or respiratory distress, etc.), and/or the like, may all be considered extreme seizure events for certain patients. Classifying a seizure event as "extreme" may be based upon an impact upon (or seriousness in relation to) the patient's health and wellbeing or the condition of the patient's disease state (e.g., a patient's epileptic disease state), or such a classification may be made in some cases based upon characteristics of the seizure event. In different cases, extreme seizure events may be classified according to other standards as well, and need not necessarily be specifically limited to those described herein. Similarly, extreme seizure events may be a combination of the above described classifications. An extreme seizure event (e.g., status epilepticus or risk of status epilepticus) may result in a pathophysiological effect in a patient such as, but not limited to damage to brain tissue resulting in permanent and/or serious damage or impairment to motor, visual, sensory and/or cognitive skills, respiratory failure, cardiac failure, pulmonary edema, cardiac arrhythmia, metabolic acidosis, liver and/or renal failure, bed sores, bone fractures, abrasions, bruises, organ or multi-organ failure, arterial hypertension, tissue hypoxia and/or tissue hypercarbia.

Whether or not the first in a chain of ultimately fatal events leading to SUDEP is a seizure, the defining event is likely to be either cardiac (e.g., ventricular fibrillation or asystole) or respiratory (e.g., apnea) or both, which in turn may be precipitated by: a) withdrawal of excitatory influences (dysfacilitation) or inhibition of the heart and/or the respiratory rhythm generators by the central autonomic network; b) Resetting of the cardiac or respiratory oscillatory phase into the so called "null-space" or "black hole", in the manner that an intense blow to the chest or lightning/electrocution causes cardiac arrest. Currently, the monitoring, detection, prediction and management (warning, treatment and prevention of death in epilepsy are underdeveloped and markedly limited in breadth and depth of scope, limitations which this invention addresses. However, this objective cannot be fulfilled unless it is taken into account (for detection and management purposes) that death in epilepsy (as discussed above) may be sudden or gradual, unexpected or expected and that observation/monitoring should take place at multiple time scales (microscopic to macroscopic as defined herein).

The following examples may add clarity and depth of detail to the critical role of "time scales" in this invention. 1. If ventricular fibrillation is the ultimate cause of sudden (very short (seconds to minutes) time window), unexpected (no history of cardiac disease), unexplained (negative autopsy findings) death, monitoring of body signal (EKG) and treatment (defibrillation) must be performed over short time scales (seconds) to prevent death or severe ischemic/hypoxic brain damage; 2. Decreases in heart rate variability (which are associated with an increased risk of sudden death) in patients with severe, long-standing epilepsy occurring gradually over months to years, require for determination that a trend exists, observation periods commensurate with said time scale, while providing longer prediction and treatment horizons that those occurring over short time scales (e.g. ventricular fibrillation). It is remarked that the embodiments described herein encompass all forms of death directly or indirectly, acutely or chronically associated with or caused by epilepsy or seizures. By way of example, tonic-clonic seizures (referred to herein as convulsions) are characterized by falls to the ground that may result in brain damage (e.g., lacerations and hemorrhage) that unless promptly recognized and treated are likely to lead to death. Through the monitoring and analyses of body signals (e.g. body position and movements) this invention will detect prolonged or unprecedented immobility (a manifestation of the brain injury) through warning and other measures, minimize the risk of death.

Classification of extreme epileptic events and risks of death may be made according to the body organ(s), body system(s) and/or index(indices) affected. The most basic classification is that of a seizure in a patient. In addition to the seizure itself, a number of body organ(s) and/or body system(s) may be affected and thus classified. A classification such as a hierarchy of impact, effect and/or importance with respect to a risk of death may be used. For example, a hierarchy of the following affected organ(s), body system(s) and/or index(indices) based on their vital role value—may be used:

I. Autonomic function(s) of a patient may be classified as, but not limited to, respiratory, cardiac and/or vascular. Body organs/systems such as the heart and blood vessels exhibit changes during seizure events, and these effects may be thus quantified, ranked and classified. Similarly, the lungs and associated metrics such as breathing patterns, tidal volume and the like may be effected and thus classified.

II. Metabolic systems and indices.
III. Tissue indices as well as tissue stress indices.
IV. Endocrine organs/systems, and their respective indices.
V. Physical fitness and integrity of the musculo-skeletal system (referred herein to as "physical fitness/integrity" and its indices.
VI. Neurologic systems and metrics such as responsiveness, awareness (or lack thereof), kinetic metrics such as immobility and cognitive metrics such as IQ and memory. Additionally or alternatively, seizure events and risks of death may be graded according to severity of risk. The levels of risk from lowest to highest may be, but are not limited to: minor, moderate, major and/or extreme. For example, any autonomic dysfunctions, such as cardiac and respiratory dysfunctions, may be graded as major given their critical and immediate role in maintaining vital functions, while specific autonomic dysfunctions such as asystole, ventricular tachycardia and ventricular fibrillation (cardiac), as well as apnea, agonal breathing, ataxic breathing, apneustic breathing and Biot's respirations may be graded as indicative of extreme risk of death. Other risk factors, such as those related to metabolic, endocrine and metabolic systems/indices, tissue stress markers and physical fitness/integrity, may be graded between minor to extreme depending on the number of organs, systems and indices involved and their respective values and rates of change. Risks of death may also be graded taking into account factors such as the age and health of the patient, wake-sleep cycle, medications, seizure impact and/or seizure burden among others. For example, a the risk associated with a 10% drop in arterial oxygen saturation occurring in a young healthy adult during wakefulness is far less serious that the same drop in an elder individual, asleep and seriously ill.

The determination of extreme seizure events, risks of death, increased risks of death and/or a risk of SUDEP may be addressed by issuing appropriate warnings to the patient, a caregiver, a physician, an EMT station, dialing 911 and/or the like. The grades for risks of death may be used, in various embodiments, to determine the type of warning issued for a given risk of death, as well as the treatment(s) provided and/or any intervention(s) given. For example, a minor risk grade may be in the case of a young healthy patient having an arterial oxygen desaturation ($SaO_2$ level) during wakefulness of 5% (from a baseline 96% to 91.2%). If a minor risk grade is determined, a warning may be issued in the form of a yellow light and/or a low audio tone, and oxygen may be administered to the patient. A moderate risk grade may be determined for a patient having a drop in $SaO_2$ level of 7% (baseline is normal) a heart rate increase of 50% and/or a blood pressure drop of 30% compared to patient's baseline values for the activity level and type, conditions, environment, etc., at/around the time of the onset of changes. If a moderate risk grade is determined, a warning may be issued in the form of an orange light and/or an audio tone of higher pitch than the minor risk grade tone, and oxygen, pressor agents and/or fluids may be administered to the patient. A major risk grade may be determined for a patient having myocardial ischemia (e.g., as evidenced by EKG or blood enzymes changes) and multifocal PVCs in addition to a drop in $SaO_2$ level of 6% in reference to the patient's baseline values for the activity level and type, conditions, environment, etc., at/around the time of the onset of changes baselines values. If a major risk grade is determined, a warning may be issued in the form of a red light and/or an audio tone of higher pitch than the moderate risk grade tone, and anti-arrhythmic therapy(ies), oxygen, pressor agents and/or fluids may be administered to the patient. An extreme risk grade may be determined for a patient having ventricular tachycardia, ventricular fibrillation and/or asystole. If an extreme risk grade is determined, a warning may be issued in the form of a purple light and/or an audio tone of higher pitch than the major risk grade tone, and defibrillation (e.g., via an activated, implantable medical device), on-demand heart pacing, anti-tachycardia pacing, oxygen, pressor agents and/or fluids may be administered to the patient. Those of ordinary skill in the art will appreciate that the values upon which the risk of death will be graded, vary among patients and within patients (intra-subject) depending on factors such as age, gender, time of day, state of health, level and type of activity, ease of access to specialized emergency care, etc., and that warnings may be issued automatically upon determination of a given risk grade. These factors may ultimately determine the grading of risk of death and action including, but not limited to, automated treatment warning and logging. The type and/or level of warning issued and the therapy may be ultimately at the discretion of the patient's physician(s) or EMT personnel.

In one or more embodiments, an oxygen saturation decreasing to an unsafe level for an otherwise physically fit epilepsy patient may be indicative of an increased risk of death for that patient. In one or more embodiments, an oxygen saturation decreasing by five percent for an epilepsy patient having one or more physical fitness/integrity deficiencies may be indicative of an increased risk of death for that patient. In one or more embodiments, a carbon dioxide build up value increasing to an unsafe level for an otherwise physically fit epilepsy patient may be indicative of an increased risk of death for that patient In one or more embodiments, a carbon dioxide build up value increasing by five percent for an epilepsy patient having one or more physical fitness/integrity deficiencies may be indicative of an increased risk of death for that patient. It should be noted that other percentage variations are contemplated for changes in oxygen saturation and carbon dioxide build up are contemplated. For example, oxygen saturation decreases of 10%, 15% 20% and/or 25% may be used in determining a risk of death. Likewise, other percentages may also be used. With respect to carbon dioxide build up, increases of 10%, 15% 20% and/or 25% may be used in determining a risk of death. Likewise, other percentages may also be used. It is also contemplated that a percentage change in oxygen saturation and/or carbon dioxide build up may be used in any patient regardless of physical fitness/integrity.

In one or more embodiments, a time scale or window may be correlated with a warning issued for a risk of death, an increased risk of death, a risk of SUDEP and/or the like. For example, based upon the type of risk (e.g., a cardiac factor such as EKG morphology, ventricular tachycardia or asystole), an indication may be made in the issued warning that is related to, or commensurate with, the time scale associated with the type of risk and the factors involved (e.g., a microscopic time scale).

In one or more embodiments, an arousal test, a responsiveness test and/or an awareness test may be administered to the patient in conjunction with, or alternatively to, the warning mechanisms described herein. responsiveness and/or an awareness tests may include, but are not limited to: an ability of a patient to reflexely react to a simple stimulus, to react to a complex stimulus, to comprehend symbols, to memorize symbols, and/or to behave adaptively. The simple stimulus may be one or more of a sensory stimulus (audio tone (e.g., high versus low pitch tones), a visual pattern stimulus, an olfactory stimulus, tactile distinction/recognition stimuli, a noxious and/or a non-noxious stimulus. The complex stimulus may be one or more of a cognitive stimuli or symbol recognition where the symbol is at least one of a verbal, geometric, graphic or visuo-spatial symbol. The adaptive behavior may be motor, psychomotor and/or cognitive.

Assessment of arousability may be performed before testing responsiveness of if the patient fails to take a responsiveness test or fails the test. Arousal stimuli may be noxious/non-noxious. Noxious stimuli may include high frequency electrical stimulation (e.g., an electrical signal at 100 Hz to activate C-fibers) delivered directly to the trigeminal ganglion, directly to a branch of the trigeminal nerve or to the skin of the patient, olfactory stimuli (e.g., smelling salts), acoustic stimuli, tactile stimuli, visual stimuli hot and/or cold temperature applications, mechanical pressure, and/or the like. If a patient fails an administered responsiveness test, any warnings, treatments and or stimuli may be continued or upgraded. If the patient passes the responsiveness test (e.g., the patient is able to complete and pass the test the first time or the patient has been aroused by the stimuli or other factors), that patient may be said to not be at risk of death and/or for SUDEP.

If the patient does not pass the responsiveness test, other indicia of responsiveness may be used to determine if the patient has is aroused. For example, body responses closely temporally correlated with the delivery of stimuli (e.g., noxious) and determining if there is a response closely temporally correlated with the stimuli and further characterizing the response if present. Muscle activity measured with EMG or body movement determined by accelerometers, EKG (e.g., tachycardia and increased respiration rate), EEG (e.g., slow to fast frequencies and/or high amplitude to low amplitude cortical signals), skin resistance (e.g., high resistance to low resistance) and/or video monitoring may be used as indicia of patient arousal. Latency, velocity, force and/or energy of responses may be used as factors for determining responsiveness. Similarly, types of movement (e.g., complex or in response to a verbal or written command, reflexive/withdrawal, or abnormal may be used as factors for determining responsiveness. While described in terms of passing and failing in various embodiments, responsiveness may also be measured in other embodiments using a scale (e.g., scale of 1 to 10 with "1" being the least responsive and "10" being the most responsive) or using existing scales.

For the purpose of embodiments presented herein, a risk of death or risk of SUDEP is treated (vide supra) as an extreme event. For simplicity of computation and by way of example, seizures whose magnitude (in one or more of the metric listed herein) exceed a measure of central tendency (e.g., mean) by more than three standard deviations, or are below the 1st percentile or 99th percentile of values, for the time of day to account for circadian variability or for state (e.g., wakefulness versus sleep) and patient may be classified as extreme. Other values for classification of events may be chosen as needed to improve performance. It should be noted, however, that in one or more embodiments no formal statistical analysis needs to be made to classify an event as extreme.

Those skilled in the art know that non-Gaussian distributions may be normalized by, for example, applying to the data logarithmic transformations so that mean, standard deviation and other measures may be estimated. The approach of treating certain seizures as extreme events lends itself to a statistical or probabilistic approach for the prevention of status epilepticus through their anticipation or early detection. The following "metrics" alone or in any combination will be used to classify a seizure or seizures into extreme as compared to non-extreme by quantifying one or more of the following:

1. Magnitude and rate of increase in seizure energy or intensity, seizure duration or extent of seizure spread (note that one type of seizure severity index may be derived from the values of at least two of these three metrics), magnitude, rate of change (e.g., drop from seizure to the post-ictal state), and/or duration in brain energy during the post-ictal state compared to a representative sample of the inter-ictal state for the patient including time of day and state (e.g., wakefulness versus sleep) and/or the rate of energy recovery from the post-ictal to the inter-ictal state; 2. Inter-seizure interval duration including the conditional probability of time to the next seizure given the time elapsed since the last seizure; 3. Seizure frequency per unit time, cumulative intensity, duration, extent, spread and/or seizure severity index (SSI) per unit time; 4. Cumulative magnitude, duration and rate of the change in post-ictal energy per unit time compared to a representative sample of the inter-ictal state for the patient including time of day and state (e.g., wakefulness versus sleep), and/or extent of spread of changes in post-ictal energy compared to a representative sample of the inter-ictal state for the patient including time of day and state (e.g., wakefulness versus sleep), 5. Magnitude and/or duration and rate of change in level of consciousness as measured using available coma scales such the Glasgow scale or qualitative classification (e.g., deep coma, superficial coma, stupor, lethargy, awake but confused) as used in clinical neurology, compared to a baseline consciousness level; 6. Magnitude, duration (when applicable, e.g., when the patient is awake) and/or rate of changes in one or more cognitive functions as measured, for example, using a reaction time or any other validated neuropsychologic test; 7. Magnitude, duration and/or rate of changes in autonomic indices such as heart rate, heart rate variability, heart rhythm, EKG, blood pressure, respirations, catecholamines, temperature and/or galvanic skin resistance, among others; 6. Magnitude, duration and/or rate of changes in metabolic indices such as arterial pH, $SaO_2$, $CO_2$, glucose and/or electrolytes, a bicarbonate (alkali acts like a pH buffer) among others; 7. Magnitude, duration and/or rates of change in endocrine indices such prolactin, cortisol, and/or growth hormone among others; and 8. Tissue stress markers such as Reactive oxygen and nitrogen species including but not limited to iso- and neuroprostanes and nitrite/nitrate ratio, gluthatione, gluthatione disulfide and gluthatione peroxidase activity, citrulline, protein carbonyls, thiobarbituric acid, the heat shock protein family, catecholamines, lactic acid, N-acetylaspartate, and metabolites of any of the foregoing tissue stress markers, free radicals, lactic acid, creatine kinase (CK), Aldolase, troponin, and/or the like.

Given that the mechanisms of SUDEP which is probably the final result of cardiac, respiratory, autonomic or neurologic dysfunction and its temporal behavior (sudden vs. gradual (e.g., minutes to hours)) have not been established and their degree of reversibility (if any), its operational definition must be stringent so as to provide ample and timely protection to the patient. For simplicity of computation, and by way of example, changes in certain indices or features indicative of the status of autonomic, neurologic, metabolic, endocrine function and of tissue stress markers, whose magnitude, rate or duration are for example two or more standard deviation above or below a measure of central tendency (e.g., mean) for certain a duration and above the 75th percentile or below the 25th percentile of values for a certain duration will be considered as indicative of an increased risk of SUDEP. Other values for standard deviation and percentiles may be chosen to improve the predictive value. The increased risk will trigger responsive actions including but not limited to warning the subject or caregivers, providing specific care (i.e., care targeted at a seizure event itself such as electrical stimulation, seizure drug treatments, and the like; cardiac defibrillation or pacing) and/or supportive care (i.e., care targeted at other patient needs such as mechanically assisting breathing (oxygen), cooling the body and/or the brain of the patient, non-seizure medications and/or drugs, fluid intake, intubation, and/or the like), and logging the type (e.g., marked bradycardia; ventricular tachycardia; cardiac ischemia; intermittent apneas with oxygen desaturation and hypercarbia; uncompensated metabolic acidosis, etc.), time of occurrence, duration, intensity/magnitude of events and their frequency/unit time, as compared to a reference value.

The following "metrics" alone or in any combination may be used to estimate the risk of death or SUDEP by way of on-line and/or off-line using implantable or non-implantable devices, continuously or intermittently. Said mortality risk (s) may be classified as Minor, Moderate, Major or Extreme using qualitative, semi-quantitatively and/or quantitatively (in a probabilistic sense) means. The "metrics" include, but are not limited to, magnitude, direction (e.g., increases or decrease), rate and type of change in:

Heart rate; heart rhythm/pattern; EKG morphology; cardiac size and ventricular wall size; cardiac motility and ejection fraction; blood pressure; cardiac tissue stress markers such as CK or troponin; respiratory rate and pattern; tidal volume; end-tidal CO2; arterial oxygen saturation; respiratory sounds; seizure energy and/or intensity, seizure duration, and/or extent of seizure spread (note that a seizure severity index may be derived from the values of at least two of these metrics); energy during the post-ictal state compared to a representative sample of the inter-ictal state for the patient including time of day and state (e.g., wakefulness versus sleep); inter-seizure interval duration including the conditional probability of time to the next seizure given the time elapsed since the last seizure; seizure frequency per unit time; cumulative intensity, duration, extent or spread or seizure severity index/unit time; duration of the change in post-ictal energy compared to a representative sample of the inter-ictal state for the patient including time of day and state (e.g., wakefulness versus sleep); extent of spread of changes in post-ictal energy compared to a representative sample of the inter-ictal state for the patient including time of day and state (e.g., wakefulness versus sleep); cumulative change in post-ictal energy compared to a representative sample of the inter-ictal state for the patient including time of day and state (e.g., wakefulness versus sleep); magnitude and duration of change in level of consciousness as measured using available coma scales such the Glasgow scale or qualitative classification (deep coma, superficial coma, stupor, lethargy, awake but confused) as may be used in clinical neurology; magnitude and duration (when applicable; e.g., patient awake) of changes in cognitive functions as measured for example using a reaction time or any other validated neuropsychologic test; arterial pH; lactate concentration; lactate/pyruvate; glucose; electrolytes; cortisol; catecholamines and/or their metabolites in body fluids; body temperature; and/or skin resistivity. Measures such as a Q-T variability index (QTvi), where $$QTvi=\log 10[(QTc/QTm2)/(RRv/RRm2)]),$$

the ratio of approximate entropy of a Q-T interval, an approximate entropy of an R-R interval (ApEnQT/ApEnRR) and/or the root mean square of successive differences between R-R interval may be also used to assess sympathetic function, risk of death and/or risk of SUDEP. QTvi is a measure of cardiac repolarization liability and may provide information about the phase in which the heart is most susceptible to cardiac arrhythmias. Abnormal QTv may be associated with ventricular arrhythmias as well as sudden cardiac death, and may provide useful information in patients with epilepsy.

In one or more embodiments, signals or markers of autonomic, neurologic, endocrine, metabolic, gastro-intestinal, and/or dermal origin and of tissue/organ stress, such as those listed below, along with processes and tools for measuring and/or deriving these signals and markers, may be indicative of seizure events, extreme seizure events and/or SUDEP:

I. Autonomic:
  a) Cardiac: Intra-cardiac pressure, cardiac volume, the ratio of intra-cardiac pressure to cardiac volume, ejection fraction, blood flow, cardiac wall temperature, heart rate variability (HRV), rate of change of HRV as a function of heart rate, heart sounds, heart rhythm, heartbeat wave morphology, point of maximum impulse force, thoracic wall deflection as measured with suitable tools such as EKG, phonocardiogram (PKG), Echocardiography, Apexcardiography (ApKG), and/or the like;
  b) Vascular: arterial and or venous pressure, arterial and/or venous blood wave pressure morphology, arterial and/or venous blood flow velocity, arterial and/or venous blood flow sounds, arterial and/or venous temperature as measured with suitable tools such as pressure, Doppler, sound, ultrasound and/or the like;
  c) Respiratory: tidal volume, minute volume, respiratory wave morphology, respiratory sounds, intercostal electromyography (EMG), diaphragmatic EMG, at least one chest wall and/or abdominal wall motion, respiratory rate (RR), rate of change of RR, arterial gases concentrations, oxygen saturation, end-tidal CO2, as measured with suitable tools;
  d) Dermal: skin resistance, skin temperature, skin blood flow, sweat gland activity as measured with suitable tools;
  e) Neurotransmitters: concentrations of catecholamines and/or catecholamine metabolites, acetylcholine and/or acetylcholinesterase activity in body fluids or other tissues with suitable assays; rate of change cathecholamines, acetylcholine and/or acetylcholinesterase activity as measured from body fluids or other tissues with suitable assays, II. Neurologic
  a) Cognitive/Behavioral: level of consciousness, level of attention, reaction time, memory, visuo-spatial, language, reasoning, judgment, calculations, auditory and/or visual discrimination as measured using validated tests;
  b) Kinetic: force of muscle contraction, body movement direction, speed, acceleration, trajectory of movements in one, two and/or three dimensions, pattern and/or quality of movements, head, eyes, limb/body posture and/or position, body part orientation and/or position in reference to each other, body part orientation and/or position in reference to one or more predetermined axes or fiducials, muscle tone, agonist-to-antagonist muscle tone ratio, gait, accessory movements, falls as measured with suitable tools;
c) Vocalizations: formed and/or unformed vocalizations as measured with suitable tools;
d) Electroencephalography (EEG), Electrocorticography (ECoG), evoked potentials, field potentials, single unit activity as measured with suitable tools, III. Endocrine:
a. prolactin, luteinizing hormone, follicle stimulation hormone, growth hormone, adreno-corticotropin hormone (ACTH), cortisol, vasopressin, beta-endorphin, beta, lipotropin, corticotropin-releasing factor (CRF) as measured from body fluids or other tissues with suitable assays;

IV. Tissue Stress Markers:
a. reactive oxygen and/or nitrogen species from the list comprising iso- and neuro-prostanes and nitrite-nitrate ratio, gluthatione, gluthatione disulfide and gluthatione peroxidase activity, citrulline, protein carbonyls, thiobarbituric acid, a heat shock protein family, catecholamines, lactic acid, N-acetylaspartate, metabolites of citrulline, protein carbonyls, thiobarbituric acid, a heat shock protein family, chromogranin A, free radicals or reactive oxygen species, catecholamines, lactic acid or N-acetylaspartate; as measured from body fluids or other tissues with suitable assays;

V. Metabolic:
a. arterial pH, arterial gases, lactate/pyruvate ratio, electrolytes and glucose as measured from body fluids or other tissues with suitable assays.

With respect detection and identification of extreme seizure events, autonomic indices, such as those described above, changes in their values (or trends in the value changes) and knowledge of the circumstances/conditions and activities of the patient may be used to estimate the likelihood and/or probability that an extreme event will occur, is occurring or has occurred. Autonomic, neurologic, metabolic, tissue stress, physical fitness/integrity and/or endocrine indices, whether extreme or otherwise, may be associated with a seizure, a post-ictal period and/or an inter-ictal period.

With respect to extreme seizure events and/or patient mortality, status epilepticus (SE) may be an independent predictor of death. As compared with a first brief epileptic seizure, an incident SE episode seems to increase the risk of developing epilepsy. Where prior studies incorrectly focused on duration of a single patient seizure, a correct approach may also include a seizure severity factor, where the seizure severity factor may be determined by a relation between the duration of a seizure, its intensity and extent of spread and its impact on autonomic (e.g., cardiac, respiratory rates and/or arterial pH), metabolic (arterial pH, lactate concentration, etc.) or other body systems. As defined herein, "extreme seizures" may be classified based on certain metrics such as, for example, a seizure severity index (SSI) and/or on the impact a seizure has on a subject, i.e., the patient impact (PSimp) or patient seizure burden. Seizure metrics may be: a) peak energy (defined for example as the product of peak intensity and duration); b) severity (defined for example as the sum of peak energies at each brain site engaged in seizure activity); and/or c) inter-seizure interval (defined as the time (in seconds or minutes) elapsed between the onset of consecutive seizures) (see Osorio et al., Epilepsia 1998; 2002; EJN, 2009; PRE 2010). Values of seizure metrics indicative of an extreme seizure may be more than two standard deviations above the mean for seizure energy or severity and below the mean for inter-seizure intervals with respect to normally distributed probability density functions. PSimp and burden are estimated or measured using neurologic, autonomic, tissue stress markers, endocrine, metabolic and musculo-skeletal signals or status. Similarly, peak intensity duration of a seizure may be used as a seizure severity factor for determining status epilepticus. An extended time spent in a seizure state, or a decreased inter-seizure interval, may be an indication of a state of status epilepticus, an impending onset of a state of status epilepticus or an increased risk for SE. Additionally, a risk of SUDEP may be identified or determined from the status epilepticus determination described above.

In one embodiment, seizure severity index (SSI) value indicative of the severity of a seizure may be determined based upon a body data. In one embodiment, the determined SSI value may be compared to reference/extreme reference values that may or may not include a status epilepticus value. The status epilepticus value(s) may be based upon at least one of a past SSI value, a mean SSI value, a median SSI value, a mode SSI value, a percentile SSI value, a normalized SSI value, a distribution of SSI values, or to any other statistical transformation of an SE index or observable SE index change.

Turning now to death and to sudden unexpected/unexplained death in epilepsy (SUDEP), dysregulation in cardiac and respiratory physiology due to seizures, dysfunction in systemic and cerebral circulation physiology due to seizures, and seizure-induced hormonal and metabolic changes may all contribute to death, risk of death, SUDEP and/or risk of SUDEP. Cardiac factors may include bradyarrhythmias and asystole, as well as tachyarrhythmias and alterations in cardiac repolarization. Altered electrolytes and blood pH, as well as the release of catecholamines, modulate cardiac excitability and might facilitate arrhythmias. Respiratory symptoms are not uncommon during seizures and comprise central apnea or bradypnea, and, less frequently, obstruction of the airways and neurogenic pulmonary edema. Alterations to autonomic function, such as a reduction in heart rate, heart rate variability (HRV) or disturbed baroreflex sensitivity, can impair the body's capacity to cope with challenging situations of elevated stress, such as seizures. A risk of death or SUDEP or increased risk of death are the most extreme of epileptic events. Ictal cardiac repolarization and rhythm abnormalities such as atrial fibrillation, premature ventricular depolarizations, marked sinus arrhythmia, premature atrial depolarizations, junctional escape, ST-segment elevation, shortening or lengthening of the QT and increased QT dispersion may all be indicia of an increased risk of death.

Seizures are powerful biological stressors and inductors of tissue stress marker indices and may deplete the body of certain anti-oxidants, such as glutathione peroxidase. Exemplary tissue stress marker indices comprise changes (direction, rate, and magnitude) in glucose, prolactin, cortisol, catecholamines, chromogranin A, free radicals or reactive oxygen species, lactic acid, blood gases, N-acetylaspartate, in the expression of heat shock proteins, and in metabolites of any or all thereof. For example, a "cortisol parameter" refers to a tissue stress marker index relating to cortisol or a metabolite thereof, and a "catecholamine parameter" refers to a tissue stress marker index relating to a catecholamine or a metabolite thereof. The concentration of certain compounds that protect from biological stress (e.g., dehydroepiandrosterone or its sulfate conjugate, glutathione peroxidase) or the body's total antioxidant capacity may be also measured to determine if it is adequate and if not to increase it using commercially or naturally available antioxidants to stall disease progression. Tissue stress marker index indices and antioxidants may be measured in brain (invasively and/or non-invasively), CSF, plasma, serum, erythrocytes, urine, and saliva (e.g. alpha amylase).

In various embodiments, approaches such as bivariate or multivariate proportional hazard regression analysis may be applied to identify factors associated with increased risk of death in patients with epilepsy. Mortality scores may be developed by assigning "points" to each factor based on either the relative risk ratio or odds ratio in the multivariate proportional analysis. The performance of this approach may be tested by measuring the area under the ROC curve (C statistic). Factors that may be entered into the risk of death (sudden unexpected, or neither sudden nor unexpected) analyses include, but are not limited to: demographic data (e.g., age, gender), body mass index, physical fitness, state of health, number of years with epilepsy, seizure frequency, time spent in seizure over a certain time window, peak seizure severity over a certain time window, cumulative seizure severity over a certain time window, maximal seizure impact, seizure burden over a certain time window, inter-seizure interval data, changes in heart rate variability, type, frequency, magnitude and duration of cardiac abnormalities during seizures and inter-ictally, type, frequency, magnitude and/or duration of elevation in stress tissue markers, quality of life (QOL), cognitive status. These data may be subjected to myriad mathematical treatments; for example, the Hurst parameter may estimated for seizure severity indices based on ictal autonomic (e.g., magnitude and duration of heart rate), neurologic (e., magnitude and/or duration of post-ictal unresponsiveness/unawareness), stress tissue factors (e.g., magnitude and duration of increases in creatine kinase (CK) or troponin associated with seizures), etc., over a certain time window (e.g., macroscopic).

Although not so limited, methods and apparatus capable of implementing embodiments of the present invention are described below. In the context of this description, a medical device (MD) or medical system may also be referred to as an implantable medical device (IMD) and/or an implantable medical device/system (MD). It is contemplated that such a device and/or system may be implantable or non-implantable/non-implanted in various embodiments without departing from the spirit and scope of the invention. That is, when an implantable medical device/system (IMD) is described in one or more embodiments, it is also contemplated that a corresponding non-implanted or non-implantable may be used in one or more alternate embodiments and vice versa. In other embodiments, some portions of the system may be implanted while other portions may be external to the patient's body.

Turning now to FIGS. 1A-1C, these drawings and MDs 100 are described in A Systems Approach to Disease State and Health Assessment (FIGS. 3A-3C) by Dr. Ivan Osorio (U.S. application Ser. No. 12/816,357), incorporated herein in its entirety. It is noted that the described MDs 100 may be implantable/implanted or non-implantable/non-implanted without departing from the spirit and scope of embodiments described herein.

It is contemplated that in various embodiments, the MDs 100 described above may be used to provide arousal stimulus to the patient as described herein. It is also contemplated that in various embodiments, the MDs 100 described above may determine arousability and/or responsiveness of a patient using the MDs 100 as coupled to the vagus nerve or a branch thereof.

Turning now to FIG. 1D, a stylized diagram of a medical device, which may or may not be implanted into a patient's body, for providing one or more stimuli to the patient, in accordance with one or more illustrative embodiments, is provided. In various embodiments, a medical device (MD) 200 may be adapted to deliver any or all of the stimuli described herein. For example, an audio stimulus may be delivered via speaker 190 or other device, a visual stimulus may be delivered to the eyes of the patient via a light source 192 or other device, an olfactory stimulus may be delivered to the nose of the patient via an olfactory stimulus device 194 or other device, and/or a pressure/mechanical stimulus and/or thermal stimulus may be delivered to the neck, ear(s), arm(s), leg(s), Achilles tendon(s), and/or the like, of the patient via a mechanical/thermal device 196 or other device. Additionally, or in the alternative, an electrical stimulus (e.g., a 100 MHz electrical pulse) may be delivered using an electrical signal generator 198 or other device via an electrical lead 199. The electrical stimulus may be delivered to the dermis, subdermis or other body location of the patient. In one embodiment, the electrical stimulus may be delivered to the face of the patient. In one embodiment, the electrical stimulus may be delivered to the heart, lungs and/or their respective systems. In another embodiment, arousal stimuli may be delivered via the vagus nerve using the therapy device. These stimuli may be in the form of high frequency and/or high intensity stimuli (so as to activate vagal pain fibers), vibrations and/or as short trains of stimuli delivered in a manner such that that they lack adverse cardiac effects.

Activation and management of the MD 200 are described in A Systems Approach to Disease State and Health Assessment (FIGS. 3A-3C) by Dr. Ivan Osorio (U.S. application Ser. No. 12/816,357). For example, a computer 188 and/or radio frequency communications device 189 may be used to facilitate delivery of various stimuli via the MD 200.

Figure 2:
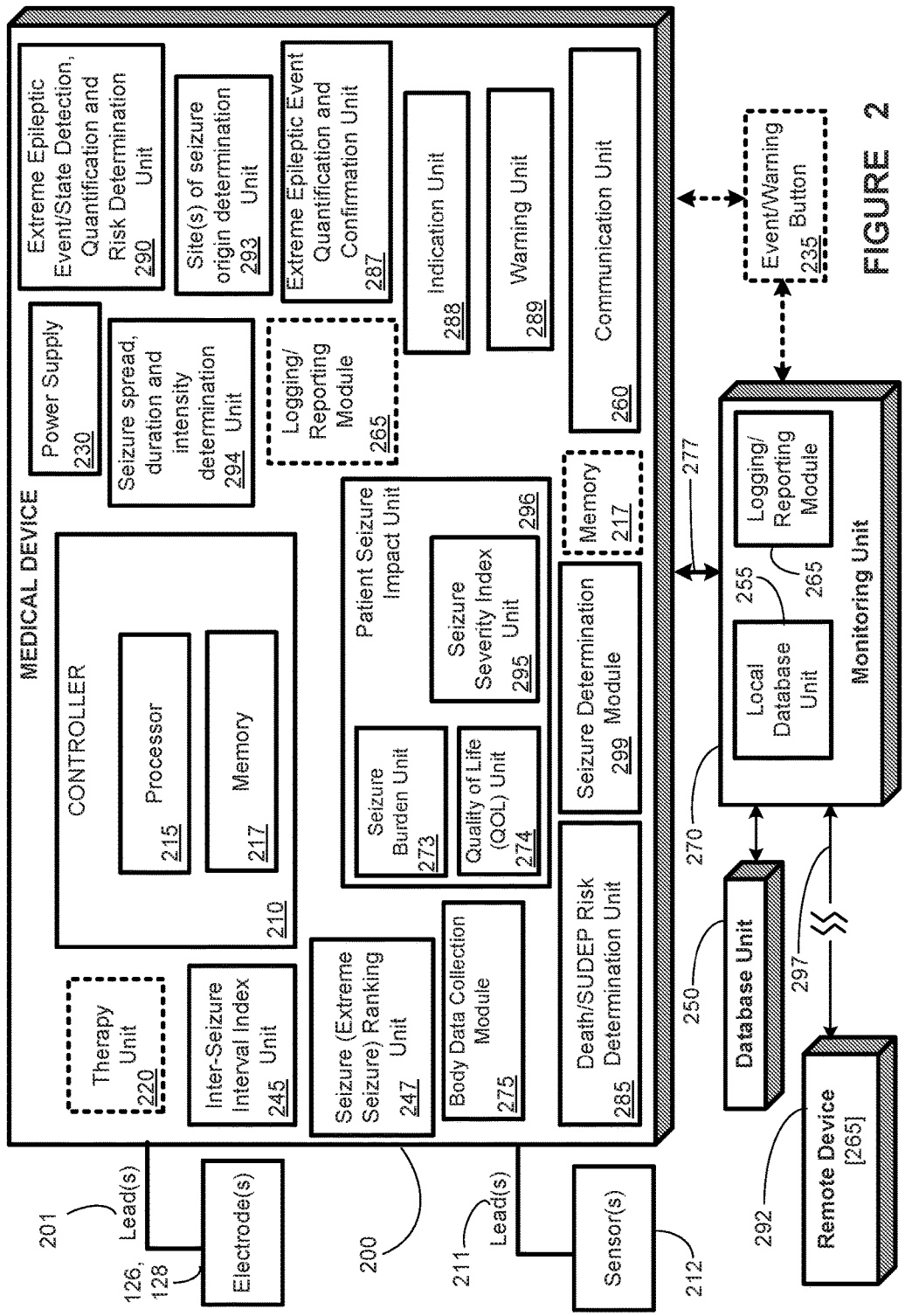
FIG. 2 illustrates a medical device for anticipating, detecting, assessing and managing (e.g., treating, warning, logging) extreme events related to epilepsy, in accordance with an illustrative embodiment of the present invention.

Turning now to FIG. 2, a block diagram depiction of a medical device (MD) 200 is provided, in accordance with one illustrative embodiment of the present invention. In some embodiments, the MD 200 may be implantable (such as implantable electrical signal generator 110 from FIG. 1), while in other embodiments the MD 200 may be completely external to the body of the patient.

The MD 200 (such as generator 110 from FIG. 1) may comprise a controller 210 capable of controlling various aspects of the operation of the MD 200. The controller 210 may include a processor 215, a memory 217, etc., for processing and storing data respectively. The processor 215 may comprise one or more microcontrollers, microprocessors, etc., capable of performing various executions of software and/or firmware components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc. In one embodiment, a memory 217 may be separate from, but communicatively coupled to the controller 210.

The controller 210 is capable of receiving internal data or external data, and in one embodiment, is capable of processing body data to identify an extreme epileptic event in a patient. For example, the controller 210 may receive data from a body data collection module 275 (described further below) or from a memory 217. Upon receiving the data or body data, the processor 215 may process the data in accordance with various embodiments described herein. For example, in one embodiment, the process may be adapted to compare values associated with two or more body data indices. The processor 215 may also provide processed data/body data to other modules and units in the MD 200. The controller 210 is capable of causing a therapy unit 220 to take responsive action in response to the identification of one or more various extreme or non-extreme epileptic events by the MD 200, or by a patient, a physician, a nurse or caregiver, etc. In one embodiment, the responsive action may comprise generating and delivering an electrical signal to target tissues of the patient's body for treating a medical condition. In one or more embodiments, the responsive action may comprise drug treatments, oxygen treatments, cooling and/or the like. For example, the controller 210 may receive manual instructions from an operator externally, or may cause the electrical signal to be generated and delivered based on internal calculations and programming. In other embodiments, the MD 200 does not comprise a therapy unit 220. In either embodiment the controller 210 is capable of affecting, and/or may be adapted to affect, substantially all functions of the MD 200.

As stated above, in one embodiment, the MD 200 may also comprise a therapy unit 220 capable of generating and delivering electrical signals to one or more electrodes 126, 128 via leads 201 (FIGS. 2B, 2D) (and/or other therapies such as drugs, thermal energy, oxygen and/or the like). A lead assembly such as lead assembly 122 (FIG. 1) may be coupled to the MD 200. Therapy may be delivered through the leads 201 comprising the lead assembly 122 by the therapy unit 220 based upon instructions from the controller 210. The therapy unit 220 may comprise various circuitries, such as electrical signal generators, impedance control circuitry to control the impedance "seen" by the leads, and other circuitry that receives instructions relating to the delivery of the electrical signal to tissue. Electrical signals delivered to a body part for therapeutic purposes may be of constant current (to compensate for impedance changes) or of constant voltage. The therapy unit 220 is capable of delivering electrical signals over the leads 201 comprising the lead assembly 122. As should be apparent, in certain embodiments, the MD 200 does not comprise a therapy unit 220, lead assembly 122, or leads 201. In particular, although FIGS. 2B and 2D are illustrated with therapy unit 220, leads 201 and electrodes 126, 128, in alternative embodiments, these structures and the stimulation function enabled thereby may be omitted.

In other embodiments, a lead 201 is operatively coupled to an electrode 126, 128, wherein the electrode 126, 128 is adapted to couple to at least one of a portion of a brain structure of the patient 190, a cranial nerve of a patient, a spinal cord of a patient 180, a sympathetic nerve structure of the patient, a peripheral nerve of the patient, a dermis and/or subdermis of a patient.

The MD 200 may also comprise a power supply 230. The power supply 230 may comprise a battery, voltage regulators, capacitors, etc., to provide power for the operation of the MD 200, including delivering the therapeutic electrical signal. The power supply 230 comprises a power source that in some embodiments may be rechargeable. In other embodiments, a non-rechargeable power source may be used. The power supply 230 provides power for the operation of the MD 200, including electronic operations and the electrical signal generation and delivery functions. The power supply 230 may comprise a lithium/thionyl chloride cell or a lithium/carbon monofluoride (LiCFx) cell if the MD 200 is implantable, or may comprise conventional watch or 9V batteries for external (i.e., non-implantable) embodiments. Other battery types known in the art may also be used.

The MD 200 may also comprise a communication unit 260 capable of facilitating communications between the MD 200 and various devices. In particular, the communication unit 260 is capable of providing transmission and reception of electronic signals to and from a monitoring unit 270, such as a handheld computer or PDA that can communicate with the MD 200 wirelessly or by cable. The communication unit 260 may include hardware, software, firmware, or any combination thereof.

The MD 200 may also comprise one or more sensor(s) 212 coupled via sensor lead(s) 211 to the MD 200. The sensor(s) 212 are capable of receiving signals related to a body parameter, such as the patient's heart beat or a body chemical, and delivering the signals to the MD 200. In one embodiment, the sensor(s) 212 may be the same as implanted electrode(s) 126, 128 (e.g., FIGS. 1A-1C). In other embodiments, the sensor(s) 212 are separate structures that may be placed on the patient's skin, such as over the patient's heart or elsewhere on the patient's body. It will be appreciated by persons of skill in the art that in some embodiments, lead 211 may be omitted and the MD 200 may communicate wirelessly with sensor 212.

The MD 200 may also comprise a body data collection module 275. The body data collection module 275 may be adapted to, and/or capable of, collecting data relating to the body of a patient. Such data may be obtained using electrical, chemical, optical, biophotonic, acoustic (e.g., ultrasound), thermal sensors, pressure sensors, bioassays, chemical methods, imaging technology and/or motion sensors in any useful combination (these measurements may be performed at one or multiple spatial scales simultaneously or sequentially (e.g., multiplexing) and include but are not limited to: 1. Neurologic data such as neuronal electrical activity, neurotransmitter concentrations and their rate(s) of release and uptake, Kreb's and other cycle compounds, other chemical compounds (e.g., electrolytes, tissue stress markers), CSF and brain tissue pressure, temperature, and/or kinematic/kinetic activity, including but not limited to posture and fine motor movements among others using imaging techniques (e.g., video), accelerometers, inclinometers, actigraph devices, and/or the like; 1a. Level of consciousness and/or cognitive signals (e.g., attention, reaction time, memory, etc.), neurological tests administered manually and/or automatically for qualitative or quantitative analyses; 2. Cardiac signals (e.g., as discussed above); 3. Body fluids signals including, but not limited to, those that may recorded using pressure, flow velocity and degree of laminarity (or turbulence) (e.g., Doppler), temperature, pH, chemical makeup (e.g., electrolytes, enzymes, tissue stress markers, anti-oxidants, gases); 4. Respiratory rate, pattern, tidal volume, and/or degree of activity of principal and/or accessory respiratory muscles to compute, for example, ratios (e.g., abdominal wall motion/thoracic wall motion, end tidal $CO_2$); 5. Endocrine indices (e.g., as discussed above); 6. Metabolic parameters (e.g., as discussed above); and 7. Kinetic data (e.g., as discussed above). This list is not exclusive, and the body data collection module 275 may collect additional data not listed herein, that would become apparent to one of skill in the art having the benefit of this disclosure. The body data collection module 275 may collect body data via one or more body data units (described in further detail below with respect to exemplary embodiments shown in FIGS. 3 & 4, [361-368]). The body data units, as shown below, may be internal to the MD 200, or external to, and communicatively coupled to, the MD 200. All data comparisons may be made taken into consideration including, but not limited to, ultradian, circadian or infradian variations, gender, body mass index, age, past and present treatments (e.g., drugs, electrical signal therapy, and/or the like), physical fitness/integrity, etc.

The body data collection module 275 may, in some embodiments, organize or process portions of the body data collected. Additionally, the body data collection module 275 may store or buffer the body data before sending the body data to other components of the MD 200. In accordance with one embodiment, the body data collection module 275 may send some or all of the body data collected by the body data collection module 275 to the controller 210 for processing. In other embodiments, the body data collection module 275 may send collected body data to other components of the medical device instead of, or in addition to, the controller 210; such other components include, but are not limited to, a SUDEP risk determination unit 285, a seizure severity ranking unit 299, a seizure severity index (SSI) unit 295 and an extreme epileptic event/state detection, quantification and risk determination unit 290. The body data collection module 275 may also send the body data to the monitoring unit 270 or remote device(s) 292 via communication unit 260.

The MD 200 may also comprise a seizure spread, duration and intensity determination unit 294. In accordance with one embodiment, the seizure spread, duration and intensity determination unit 294 may determine the amount of spread the seizure event and/or extreme seizure event. In other words, the greater the seizure spread, the more areas of the brain and/or body organs are affected by the seizure event and/or extreme seizure event. The seizure spread, duration and intensity determination unit 294 may make such a determination based upon body data information, external indications, and/or other data that would become apparent to one of skill in the art having the benefit of this disclosure.

The seizure spread, duration and intensity determination unit 294 may be adapted to provide seizure duration data which may include the duration of a patient's seizure event. The duration of a seizure event may be determined as the time that any of the autonomic, neurologic, metabolic, endocrine, or stress tissue marker indices values differ from inter-ictal and/or post-ictal values. In some embodiments, electrographic or clinical onset may be approximated by other body parameters, e.g., heart rate, kinetic activity, etc. In alternative embodiments, the duration of a seizure event may be determined as the time a body data value, a site(s) data value and/or an intensity, duration and spread data value (or value(s) respectively related thereto) is above or below adaptable and/or pre-determined threshold(s) and/or separatrix(tices). In further embodiments, the duration of a seizure event may be based on other criteria as would be apparent to one of skill in the art having the benefit of this disclosure. The seizure spread, duration and intensity determination unit 294 may also be adapted to determine a time spent in a seizure event state over a given time period or window (e.g., macroscopic as defined above); such a determination may include one or more seizure events occurring within the time period (as discussed in further detail below with respect to FIG. 13). The time periods/windows may be of a fixed duration or may be of adjustable duration; likewise, the time period or window may move with or without overlap.

The seizure spread, duration and intensity determination unit 294 may be adapted to provide seizure intensity data which may include the energy associated with a patient's seizure event. As described above, seizure intensity may be defined as the value of any one, or any number, of body data values during a seizure event. A maximum intensity of a seizure may be defined as the maximum value of any one, or any number, of body data values during a seizure event (e.g., the maximum heart rate of a patient during a seizure event).

The MD 200 may also comprise a seizure severity index (SSI) unit 295. SSIs may be calculated in some embodiments using at least two of seizure intensity, duration or extent of spread and using at least of one autonomic, endocrine, metabolic, stress tissue marker signals. For example, SSI may be the product of intensity and spread or the sum of intensity, duration and spread using one or more organ/system indices. In accordance with one embodiment, the SSI unit 295 may determine one or more seizure severity indices (SSIs) based upon the body data collected by the body data collection module 275 and/or other relevant data. An SSI may be a scalar-valued function of one or more body data variables that simplifies a possibly complex set of body information down to a single number: the SSI. In accordance with one embodiment, the SSI may be any statistic (or scalar-valued function) associated with a seizure with the property values that reflect some aspect of the severity of the corresponding seizures and may be ordered/sorted so that the distance between the SSI values for different seizures can be measured, compared and/or interpreted to provide meaningful information. In one embodiment, the SSI may be a quantity whose variation over a period of time measures the change in some body data or body phenomenon. In one embodiment, the SSI may be intended to generally reflect the impact of a seizure on a body organ or system. The SSI may also be a statistic associated with the seizure that enables comparison between different seizures, and the values for different seizures may be ordered/sorted and the distance (in a Euclidian or non-Euclidian sense) between them measured/compared/interpreted to provide meaningful information. If the SSI values describe the severity of the seizure not in absolute terms, but in a manner relative to other seizures for that patient (or relative to other patients), the SSI may be referred to as a "Relative SSI." Additionally, when more than one SSI is used at the same time, the plurality of SSIs may be combined into a single SSI by weighted averaging, and/or the like.

The MD 200 may also comprise an inter-seizure interval index unit 245. In accordance with one embodiment, the inter-seizure interval index unit 245 may determine an index based upon inter-seizure interval. The inter-seizure interval index may, in some embodiments, be representative of the current inter-seizure interval relative to past single values, sets or values or value distributions and/or expected inter-seizure intervals, either for a specific patient or for one or more patients or patient populations. The inter-seizure interval index unit 245 may make such rankings based upon body data information, external indications (e.g., the patient's environment or surroundings), a patient's past seizure data, a normalized seizure data distribution, expected seizure data and/or other data that would become apparent to one of skill in the art having the benefit of this disclosure. Additionally, the inter-seizure interval index unit 245 may base its index upon a comparison of any or all of the above referenced data, information or indications.

Inter seizure intervals (ISIs), post-ictal severity indices (PISIs), seizure severity indices (SSIs) and patient seizure impact (PSimp) may be used alone or in combination to determine the probability that an extreme event will occur, is occurring or has occurred. These data may be derived using one or more autonomic (e.g., cardiac, respiratory, dermal), endocrine (e.g., prolactin), metabolic (e.g., arterial pH), tissue stress markers (e.g., CK) or neurologic (e.g., kinetic, cognitive) signals.

In one more embodiments identifying an occurrence of an extreme event with a certain probability or an increased risk of an extreme event state with a certain probability may be based upon a comparison of a determined SSI, ISI or PSimp values or upon models based, among others, on the temporal evolution of SSI, ISI or PSimp (for a specific patient or patient populations) in any combination.

The MD 200 may also comprise a seizure (extreme seizure) ranking unit 247. In accordance with one embodiment, the seizure (extreme seizure) ranking unit 247 may determine a ranking of a seizure event and/or extreme seizure based upon severity, ISI, PISI, PSimp, PSB and/or other factors. In one or more embodiments, the seizure (extreme seizure) ranking unit 247 may rank either seizure events or extreme seizure events. That is, in various embodiments, the seizure (extreme seizure) ranking unit 247 may be used for ranking one of seizure events or extreme seizure events. Alternatively, in one embodiment, multiple instances of the seizure (extreme seizure) ranking unit 247 may be implemented in the MD 200 (e.g., one instance for ranking seizure events and one instance for ranking extreme seizure events). As such, specific determinations relative to seizure events and/or extreme seizure events may be made independently of each other. For instance, a library or report log of just extreme seizure events may be maintained; this may allow for extreme seizure event comparisons and rankings which need not include non-extreme seizure events.

The ranking of seizure events and/or extreme seizure events may, in some embodiments, be based upon a reference value that may in turn be based upon normative, reference and/or historical patient data, or the like, which may be patient-specific or for particular patient populations. In the case of extreme events, an extreme reference value may be used. An extreme reference value may be a reference value above and beyond that used to indicate non-extreme seizure events. In other words, the seizure (extreme seizure) ranking unit 247 may make such rankings based upon body data information, external indications, a patient's past seizure data and/or other data that would become apparent to one of skill in the art having the benefit of this disclosure. Additionally, the seizure (extreme seizure) ranking unit 247 may base its ranking(s) upon a comparison of any or all of the above referenced data, information or indications.

The MD 200 may also comprise a site(s) of seizure origin determination unit 293. In accordance with one embodiment, the site(s) of seizure origin determination unit 293 may determine the site or sites of origin of a seizure event and/or extreme seizure event in a patient's brain. This information may be used to determine different types of seizure events, rank them according to severity (SSI), ISI, PISI, PSimp and/or PSB according to site of origin and classify them as extreme or non-extreme events. The site(s) of seizure origin determination unit 293 may make such a determination based upon body data information, external indications, and/or other data that would become apparent to one of skill in the art having the benefit of this disclosure. In one embodiment, patients in whom seizures originate from more than one brain site ("focus") within a region, one region in a lobe, one lobe within a hemisphere and/or one hemisphere, SSI, ISI, PISI, PSimp and/or PSB values may be determined from each site, region, lobe and/or hemisphere by performing statistical analyses to obtain measures of central tendency (e.g., mean), distributions (either temporal, spatial or both), and comparing the determined SSI value to reference/extreme reference value(s) that may or may not include a status epilepticus value. The status epilepticus value may be based upon at least one determination of if a status epilepticus event is occurring or the probability that it may occur.

The MD 200 may also comprise a seizure determination module 299. In accordance with one embodiment, the seizure determination module 299 may determine whether or not a patient has had, or is having, a seizure/extreme seizure event using body data. The seizure determination module may make such a determination based upon body data information, external indications, and/or other data that would become apparent to one of skill in the art having the benefit of this disclosure.

The MD 200 may also comprise a patient seizure impact (PSimp) unit 296. In accordance with one embodiment, the PSimp unit 296 may determine one or more seizure impact indices (PSimps) based upon the body data collected by the body data collection module 275 and/or other relevant data. IO: redundant The PSimp provides information not contained in the SSI (or in the inter-seizure interval index (ISI)) with regard to the effect of a seizure upon one or more body organs or parts. Two seizures (e.g., convulsions) with identical SSI may have a different impact on a patient: If during one such seizure (SSI=2200) the patient is walking downstairs, falls down suffers skull and rib fractures and brain contusions and during another seizure (SSI=2200) the patient is sitting down and drops onto a carpeted floor and does not suffer any injuries, the PSimp of the first seizure is considerable higher than that of the second one. Yet another example may be a patient whose overall health and body state is diminished by successive, similar seizure events and/or extreme seizure events after which the patient is not able to return to baseline with respect to one or more body parameters. Given the patient's diminished state, a subsequent, similar seizure event and/or extreme seizure event may have a more detrimental impact upon the patient than the previous, similar seizure events and/or extreme seizure events.

The PSimp may be a function of a patient's health, age, physical fitness/integrity, circumstances, conditions and activities the patient is performing as a seizure occurs. That is, PSimp, depends on the time of day (day vs. night) patient's body state (e.g., body position), condition of one or more organ(s), level of physical activity (e.g., running vs. lying down), location of the patient (swimming in a pool vs. lying down in bed), state of alertness (awake vs. asleep), and the like.

In accordance with one embodiment, the PSimp may be any statistic (or scalar-valued function) that reflect some aspect of the impact of seizures on a patient and may be sorted out and ranked so that the PSimp for different seizures can be measured, compared and/or interpreted to provide meaningful information. If the PSimp values describe the impact of the seizure not in absolute terms, but in a manner relative to other seizures for that patient (or relative to other patients), the PSimp may be referred to as a "Relative PSimp." Additionally, when more than one PSimp is used at the same time, the plurality of PIs may be combined into a single PSimp by weighted averaging, and/or the like. Furthermore, the PSimp alone (e.g., independent of SSI or ISI) may determine whether or not a seizure event is classified as extreme. In the example above, while the two seizures' SSIs are identical (2200), the one associated with bone fractures and brain contusion is extreme while the other is not. The PSimp value may be indicative of a risk of extreme events or states such as status epilepticus, SUDEP, body injuries and/or the like.

In one embodiment, the PSimp unit 296 may be adapted to perform a method, comprising receiving body data relating to at least one of an autonomic signal, a neurologic signal, an endocrine signal, a metabolic signal, or a body injury scale; identifying a seizure event based upon said body data; determining at least one PSimp value (quantitatively or qualitatively) reflective of the severity of said seizure event based at least upon said body data; comparing said determined at least one PSimp value to at least one reference value or extreme reference value; and identifying at least one of an occurrence of an extreme seizure event or an occurrence of a non-extreme seizure event, said identification being based upon at least the comparison of said determined PSimp value to said at least one reference value or extreme reference value. The SSI unit 295, which may be incorporated into the PSimp unit 296 in one or more embodiments, may be adapted to and/or be capable of making a qualitative assessment of the PSimp value, such as: non-existent, mild, moderate and severe. The SSI unit 295 may be adapted to and/or be capable of determining a scaled value associated with said PSimp value based at least upon a quantitative assessment of the PSimp value; and assigning said PSimp value to a PSimp ranking unit.

The PSimp also increases specificity of event detection and getting performance closer to the goal of "zero false positives." That is, if a seizure event and/or an extreme seizure event impacts a patient, the seizure event and/or an extreme seizure event would be unequivocally detected and/or identified. The impact of a seizure event and/or an extreme seizure event may be detected in any number of ways. In other words, even if a seizure event and/or an extreme seizure event is not detected based upon metrics based for example on heart rate and respirations directly indicative of an ictal state, its impact on the patient's health or quality of life (QOL) and mental health, would be detectable. This indirect impact may or may not be perceived by the patient or the caregivers but it may be determined, logged and recorded in one embodiment of this invention. For example, cumulative decline in heart rate variability as a function of recurring seizures, a change associated with an increased mortality risk that cannot be perceived by the patient or by caregivers without resorting to sophisticated statistical analyses, may be tracked, quantified, logged and recorded in one embodiment of this invention. Similarly, other unperceived extreme metrics may be quantified in addition to, or instead of, the logging of the impact and/or PSimp value.

In one or more embodiments, the PSimp unit 296 may also comprise a patient seizure burden (PSB) unit 273 adapted to determine a seizure burden on the patient and in another embodiment the PSB unit 273 may be separate from the PSimp unit 296. PSB is determined by measuring the magnitude of change (e.g., decline), rate of change of any and all of body organs/systems through analysis of any or all of their indices. PSB may be also determined by identifying the appearance of abnormalities in any body organs/systems, quantifying them and logging the results and time of occurrence of changes for future comparisons. For example, a highly relevant neurologic index, such as memory may be measured over time using validated tests and the scores may be used to determine if there is deterioration in this index, its magnitude and rate of change. In one embodiment, statistical analysis (e.g. regression analysis) may be performed to better identify the seizure contribution to the deterioration in certain or to the appearance of abnormalities (e.g. multi-focal PVCs). To this end, the indices used to measure PSB are for example correlated with the sum of SSI values over a time window (e.g., macroscopic) or a window based on some other time scale, or with the sum of SSI values per unit time multiplied by the time spent in seizure per unit time. Other means to determine the role of seizure in the patient's deterioration are: a) the sum of SSI values over a time window divided by mean or median inter-seizure interval (ISI) value over that time window; b) the sum of SSI and post-ictal severity indices (PISI) over a time window or the sum of SSI and PISI multiplied by the sum of times spent in the seizure and post-ictal states over that time window; c) Seizure temporal density defined as the time spent in seizure over a time window divided by the number of seizure events over that time window; d) a product of time spent in seizure and the mean or median SSI value over that time window, divided by the number of seizures over that time window; e) the relation of an SSI or ISI value to other values/measures at different times. It should be noted that seizure burden may vary due to the time of day/night: one or more extreme/non-extreme values may be chosen as a reference value for times of sleep or wakefulness. That is, when calculating and comparing a seizure burden, it may be useful to compare the seizure burden value to one obtained at same time of day or state (i.e., morning to morning, sleep-to-sleep and/or resting to resting).

In addition to the PSimp and PSB measures, comparisons of SSI, PISI and/or ISI values to historical values allows quantification of the evolution of epilepsy as a function of time, therapies and preventive measures. For example, by plotting SSI values on the y-axis over a time window (x-axis) trends in the direction of improvement, worsening or stabilization of epilepsy may be easily determined. Increases in SSI or PISI values and/or decreases in ISI as a function of treatment may require a warning and appropriate therapy/treatment.

In another embodiment, a quality of life (QOL) unit 274 may be incorporated into the PSimp unit 296 to determine the impact of epilepsy and seizures on a patient's QOL. The QOL unit 274 may be adapted to determine/quantify one or more QOL factors for a patient, such as mood, sense of well-being (or lack of it thereof), sexual activity and/or the like. The determination of various QOL factors may be used in the calculation/determination of PSB. In yet another embodiment, the physical fitness/integrity index unit 355 and the physical fitness/integrity determination unit 376 may be incorporated into PSimp unit 296 or in into a PSB unit 273 to determine the impact of the physical fitness/integrity index on the PSB. Decreases in fitness/integrity as documented using fitness/integrity measures may be correlated for example with SSI as detailed above to determine its contribution to loss of fitness/integrity).

The MD 200 may also comprise an extreme epileptic event/state detection, quantification and risk determination unit 290. In accordance with one embodiment, the extreme epileptic event/state detection, quantification and risk determination unit 290 may determine a current state and/or a future risk of entering a status epilepticus state. In one embodiment, the extreme epileptic event/state detection, quantification and risk determination unit 290 may identify a status epilepticus event from a group consisting of a present status epilepticus state, a past status epilepticus state or an increased risk of a status epilepticus state. The determination and/or identification of a risk/state of an extreme event such as status epilepticus may be made based in part or whole upon a comparison of one or more SSI, PISI and/or ISI values to a status epilepticus threshold value(s) or to a reference/extreme reference value that may in turn be based upon reference, normative and/or historical patient data, or the like.

The MD 200 may also comprise an extreme epileptic event confirmation unit 287. In accordance with one embodiment, the extreme epileptic event confirmation unit 287 may confirm that a patient is having an extreme epileptic event and that said event is status epilepticus. The extreme epileptic event quantification and confirmation unit 287 may also confirm that a patient remains in a state of status epilepticus subsequent to an initial detection/identification of the state of status epilepticus.

The MD 200 may also comprise a state assessment unit 288. In accordance with one embodiment, the state assessment unit 288 may indicate various states of a patient's disease, including but not limited to, a status epilepticus event, a risk of SUDEP, a current seizure event, variations in body data indicative of an event/change of a patient's disease state, and the like. In one embodiment, the indication may be provided to other components within the MD 200, to the monitoring unit 270 and/or database unit 250 and/or local database unit 255, to a remote device 292, to the PSimp unit 296, to the PSB unit 273, to a patient, to a caregiver or physician, or the like. The state assessment unit 288 may further indicate that the state or change in state of the patient's disease should be logged, for example, in database unit 250, local database unit 255, and/or the like.

The MD 200 may also comprise a warning unit 289. In accordance with one embodiment, the warning unit 289 may issue a warning to a patient, physician and/or care giver. Such a warning may be indicative of various states of a patient's disease, including but not limited to, an extreme epileptic event such as status epilepticus, a risk of SUDEP, a current seizure event, variations in body data indicative of an event/change of a patient's disease state, and the like, as described above with respect to the state assessment unit 288. Additionally, the warning unit 289 may warn that an event presents an increased risk to the health and/or safety of the patient. The warning unit 289 may provide a warning for a patient, physician and/or care giver to take some immediate or otherwise urgent action related to the event/change of a patient's disease state. The warning unit 289 may warn in addition, or alternatively, to the indication provided by the state assessment unit 288 described above.

The MD 200 may also comprise an event/warning button 235. In accordance with one embodiment, the event/warning button 235 may be located external to the MD 200 in an implanted/non-implanted embodiment, or may be part of the MD 200 in non-implanted embodiments. The event/warning button 235 may be communicatively coupled to the MD 200 and/or to the monitoring unit 270 in various embodiments. The event/warning button 235 may allow for a patient or other individual (such as a caregiver, family member or emergency response personnel) to activate a warning to identify a seizure event and/or an extreme seizure event/state. Such activation may be used to warn of, treat and/or log a seizure event and/or an extreme seizure event/state. Additionally, in one or more embodiments, the event/warning button 235 may be used to elevate a warning or therapy for an existing seizure event and/or an extreme seizure event/state.

In addition to components of the MD 200 described above, a non-implantable/implantable medical system may comprise a storage unit to store an indication of at least one of epilepsy event (e.g., a seizure or an increased risk of a seizure). The storage unit may be the memory 217 of the MD 200, another storage unit of the MD 200, or an external database, such as the local database unit 255 or a remote database unit 250. The MD 200 may communicate the indication via the communications unit 260. Alternatively or in addition to an external database, the MD 200 may be adapted to communicate the indication to at least one of a patient, a caregiver, or a healthcare provider.

In various embodiments, one or more of the units or modules described above may be located in a monitoring unit 270 or a remote device 292. For example, in one exemplary embodiment, the extreme epileptic event/state detection, quantification and risk determination unit 290 may be external to the MD 200, e.g., in a monitoring unit 270 or a remote device 292. Locating the extreme epileptic event/state detection, quantification and risk determination unit 290 outside the MD 200 may be advantageous if the status epilepticus risk determination or detection parameter calculation is computationally intensive, in order to reduce energy expenditure and heat generation in the MD 200 or to expedite calculation of the at least one status epilepticus risk determination or detection parameter.

The monitoring unit 270 may be a device that is capable of transmitting and receiving data to and from the MD 200. In one embodiment, the monitoring unit 270 is a computer system capable of executing a data-acquisition program. The monitoring unit 270 may be controlled by a healthcare provider, such as a physician, remotely at a base station, for example, from a doctor's office or also directly. In alternative embodiments, the monitoring unit 270 may be controlled by a patient in a system providing less interactive communication with the MD 200 than another monitoring unit 270 controlled by a healthcare provider. Whether controlled by the patient or by a healthcare provider, the monitoring unit 270 may be a computer, preferably a hand-held computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 270 may download various parameters and program software into the MD 200 for programming the operation of the medical device, and may also receive and upload various status conditions and other data from the MD 200. Communications between the monitoring unit 270 and the communication unit 260 in the MD 200 may occur via a wireless or other type of communication, represented generally by line 277 in FIG. 2. This may occur using, e.g., a wand 155 to communicate by RF energy with an MD 200. Alternatively, the wand may be omitted in some systems, e.g., systems in which the MD 200 is non-implantable, or implantable systems in which monitoring unit 270 and MD 200 operate in the MICS bandwidths.

Likewise, in various embodiments the remote device 292 may communicate with the monitoring unit 270, and thus with the MD 200, with communications between the remote device 292 and the monitoring unit 270 represented generally by line 297 in FIG. 2. Communications between the monitoring unit 270 and the remote device 292 may occur via a wireless or other type of communication represented by line 277.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting thresholds for one or more event detection parameters) using the monitoring unit 270, which may include obtaining and/or analyzing data from the MD 200 and/or data from the database unit 250 and/or the local database unit 255. The database unit 250 and/or the local database unit 255 may store various patient data.

The MD 200 may also comprise a logging/reporting module 265. The logging/reporting module 265 may be adapted to log and/or store data related to the patient, the patient's physical condition, the patient's disease and disease state and/or any other body data. The logging/reporting module 265 may be adapted to log and/or store information indicative of events relating to the patient's epilepsy disorder (e.g., seizure events, data related to time of recovery after seizure events and/or patient sleep-wake cycles) or to a concurrent disease or co-morbidity. The logging/reporting module 265 may also be adapted to log and/or store a timestamp indicative of the time and day on which stored data is/was acquired. The logging/reporting module 265 may also be adapted to log and/or store various data, as described herein, for a predetermined time period before and/or after seizure events and the like. That is, the logging/reporting module 265 may buffer data as it is acquired (e.g., in time windows of 30 seconds, 1 minutes, 2 minutes, 5 minutes or 10 minutes) and log/store the buffered data if a seizure event or other event of interest occurs within a given time window. The logging/reporting module 265 may be adapted to report stored data, or any portion thereof, to a patient, a physician, a care giver, an external computer 150, a database unit 250, a local database unit 255 and/or a remote device 292. It is contemplated that the logging/reporting module 265 may not be present in the MD 200 in various embodiments, or alternatively, that the logging/reporting module 265 may be located in a monitoring unit 270 or a remote device 292.

One or more of the blocks illustrated in the block diagram of the MD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units from the various blocks illustrated in FIG. 2 may be combined into a programmable device, such as a field programmable gate array, an ASIC device, etc.

The medical device system, in one exemplary embodiment, provides for software module(s) that are capable of acquiring, storing, and processing various forms of data, such as patient data/parameters (e.g., body data such as heart rate, breathing rate, brain-activity parameters, PSimp data, PSB data (e.g., disease progression or regression data, quality of life data, etc.), and/or the like) as well as therapy parameter data (e.g., adverse effects). Therapy parameters may include, but are not limited to, electrical signal parameters that define therapeutic electrical signals delivered by the medical device in response to the detection of an epilepsy event, medication parameters and/or any other therapeutic treatment parameter. Therapy parameters for a therapeutic electrical signal may also include, but are not limited to, a current amplitude, a pulse width, a pulse shape, a frequency, an on-time, an off-time, etc.

In one exemplary embodiment, at least one electrode may be coupled of to each of two or more cranial nerves. (In this context, two or more cranial nerves mean two or more nerves having different names or numerical designations, and do not refer to the left and right versions of a particular nerve. However, bilateral (left and right) stimulation of the same nerve may be also carried out). In one embodiment, at least one electrode may be coupled to either or both vagus nerves or a branch of either or both vagus nerves. The term "operatively" coupled may include direct or indirect coupling. Each of the nerves in this embodiment or others involving two or more cranial nerves may be stimulated according to particular activation modalities that may be independent between the two nerves. In another embodiment, a therapy may be delivered directly to the brain.

Figure 3:
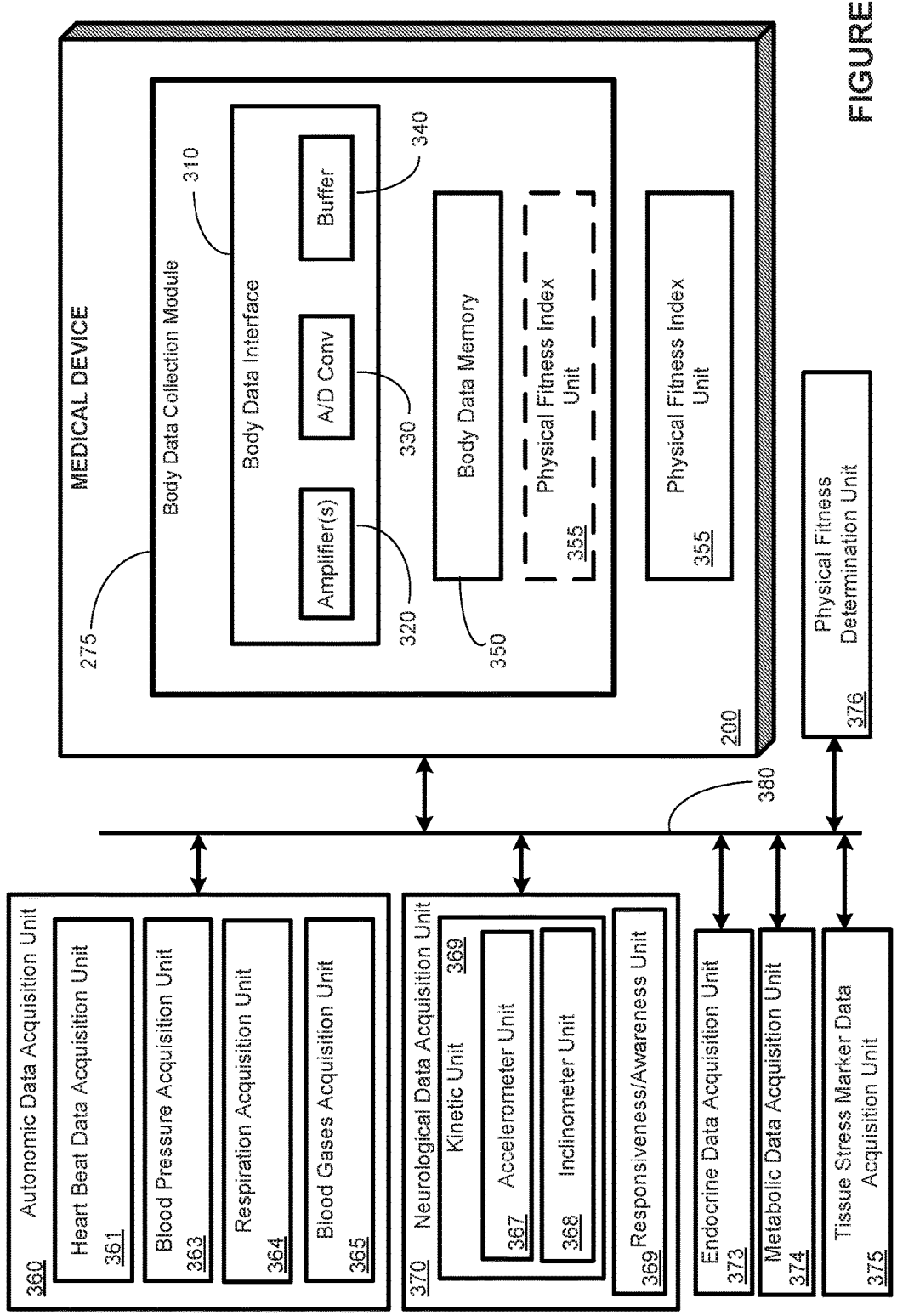
FIG. 3 provides a stylized diagram of a medical device and its different data acquisition units that may be implanted into a patient's body, in accordance with one illustrative embodiment of the present invention.

Turning now to FIG. 3, a block diagram depiction of an MD 200 is provided, in accordance with one illustrative embodiment of the present invention. FIG. 3 depicts an exemplary implementation of the body data collection module 275 described above with respect to FIG. 2. The body data collection module 275 may include hardware (e.g., amplifiers, accelerometers), tools for chemical assays, optical measuring tools, a body data memory 350 for storing and/or buffering data in the body data collection module 275. The body data memory 350 may, in some embodiments, be adapted to store body data for logging or reporting purposes and/or for future body data processing and/or statistical analyses. The body data collection module 275 may also include one or more body data interfaces 310. The body data interface 310 may provide an interface for input/output (I/O) communications between the body data collection module 275 and body data units/modules (e.g., [360-370], [373-376]) via connection 380. Connection 380 may be a wired or wireless connection, or a combination of the two. The connection 380 may be a bus-like implementation or may include an individual connection (not shown) for each, or some number, of the body data units (e.g., [360-370], [373-376]). The connection 380 may also include connection elements as would be known to one of skill in the art having the benefit of this disclosure. In various embodiments, the body data units may include, but are not limited to, an autonomic data acquisition unit 360, a neurologic data acquisition unit 370, and endocrine data acquisition unit 373, a metabolic data acquisition unit 374, a tissue stress marker data acquisition unit 375, a QOL unit 274 and/or a physical fitness/integrity acquisition and determination unit 376. In one embodiment, the autonomic data acquisition unit 360 may include a heart beat data acquisition unit 361 adapted to acquire a phonocardiogram (PKG), EKG, echocardiophraphy, apexcardiography and/or the like, a blood pressure acquisition unit 363, a respiration acquisition unit 364, a blood gases acquisition unit 365, and/or the like. In one embodiment, the neurologic data acquisition unit 370 may contain a kinetic unit 366 that may comprise an accelerometer unit 367, an inclinometer unit 368, and/or the like; the neurologic data acquisition unit 370 may also contain a responsiveness/awareness unit 369 that may be used to determine a patient's responsiveness to testing/stimuli and/or a patient's awareness of their surroundings. These lists are not exclusive, and the body data collection module 275 may collect additional data not listed herein, that would become apparent to one of skill in the art having the benefit of this disclosure. The body data units ([360-370], [373-376]) may be adapted to collect, acquire, receive/transmit heart beat data, EKG, PKG, echocardiogram, apex-cardiogram, blood pressure, respirations, blood gases, body acceleration data, body inclination data, EEG/ECoG and/or the like.

The body data interface(s) 310 may include various amplifier(s) 320, one or more A/D converters 330 and/or one or more buffers 340 or other memory (not shown). In one embodiment, the amplifier(s) 320 may be adapted to boost and condition incoming and/or outgoing signal strengths for signals such as those to/from any of the body data units/modules (e.g., ([360-370], [373-376])) or signals to/from other units/modules of the MD 200. The A/D converter(s) 330 may be adapted to convert analog input signals from the body data unit(s)/module(s) into a digital signal format for processing by controller 210 (and/or processor 215). A converted signal may also be stored in a buffer(s) 340, a body data memory 350, or some other memory internal to the MD 200 (e.g., memory 217, FIG. 2) or external to the MD 200 (e.g., monitoring unit 270, local database unit 255, database unit 250, remote device 292). The buffer(s) 340 may be adapted to buffer and/or store signals received by the body data collection module 275 as well as signals to be transmitted by the body data collection module 275. In various embodiments, the buffer(s) 340 may also be adapted to buffer and/or store signals in the body data collection module 275 as these signals are transmitted between components of the body data collection module 275.

As an illustrative example, in one embodiment, data related to a patient's respiration may be acquired by respiration unit 364 and sent to the MD 200. The body data collection module 275 in the MD 200 may receive the respiration data using body data interface(s) 310. As the data is received by the body data interface(s) 310, the incoming data may be amplified/conditioned by amplifier(s) 320 and then converted by A/D converter(s) into a digital form. The digital signal may be buffered by a buffer(s) 340 before the data signal is transmitted to other components of the body data collection module 275 (e.g., body data memory 350) or other components of the MD 200 (e.g., controller 210, processor 215, memory 217, communication unit 260, seizure determination module 299, SSI unit 295, extreme epileptic event/state detection, quantification and risk determination unit 290, or the like). Body data in analog form may be also used in one or more embodiments.

Figure 4:
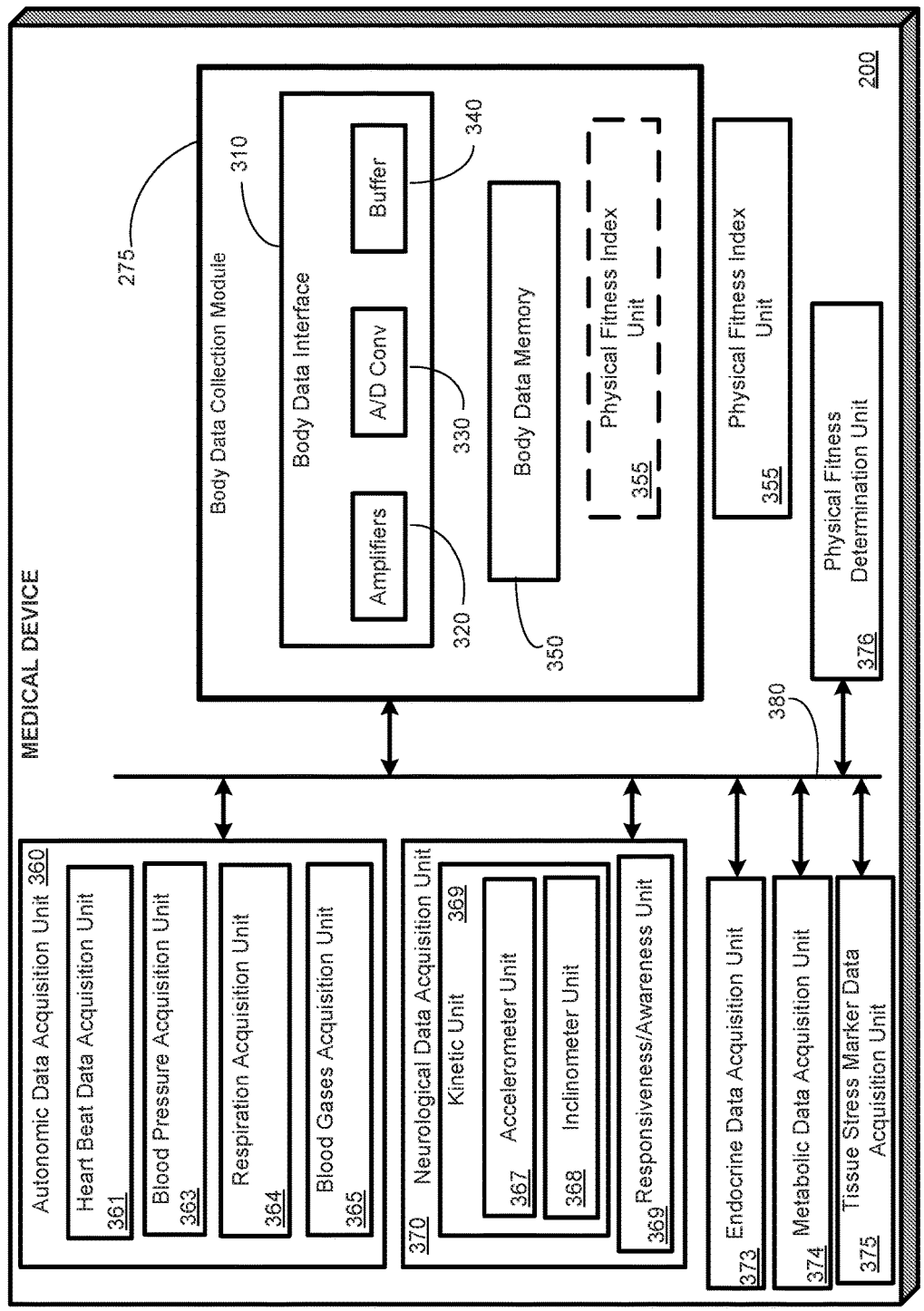
FIG. 4 provides a stylized diagram of a medical device which may be implanted into a patient's body, in accordance with one illustrative embodiment of the present invention.

Turning now to FIG. 4, an MD 200 (as described above in FIG. 3) is provided, in accordance with one illustrative embodiment of the present invention. FIG. 4 depicts the body data units (FIGS. 3 & 4, [360-370], [373-376]), in accordance with one embodiment, being externally coupled to the MD 200, instead of being included within the MD 200 as shown in FIG. 3. In accordance with various embodiments, any number and type of body data units (FIGS. 3 & 4, [360-370], [373-376]) may be included within the MD 200, as shown in FIG. 4 while other body data units (FIGS. 3 & 4, [360-370], [373-376]) may be externally coupled, as shown in FIG. 3. The body data units (FIGS. 3 & 4, [360-370], [373-376]) may be coupled to the body data collection module 275 in a fashion similar to that described above with respect to FIG. 3 (380), or in any number of different manners used in coupling intra-medical device modules and units. It should be noted that the manner by which the body data units (FIGS. 3 & 4, [360-370], [373-376]) may be coupled to the body data collection module 275 is not essential to and does not limit the embodiments described herein as would be understood by one of skill in the art having the benefit of this disclosure.

Figure 5A:
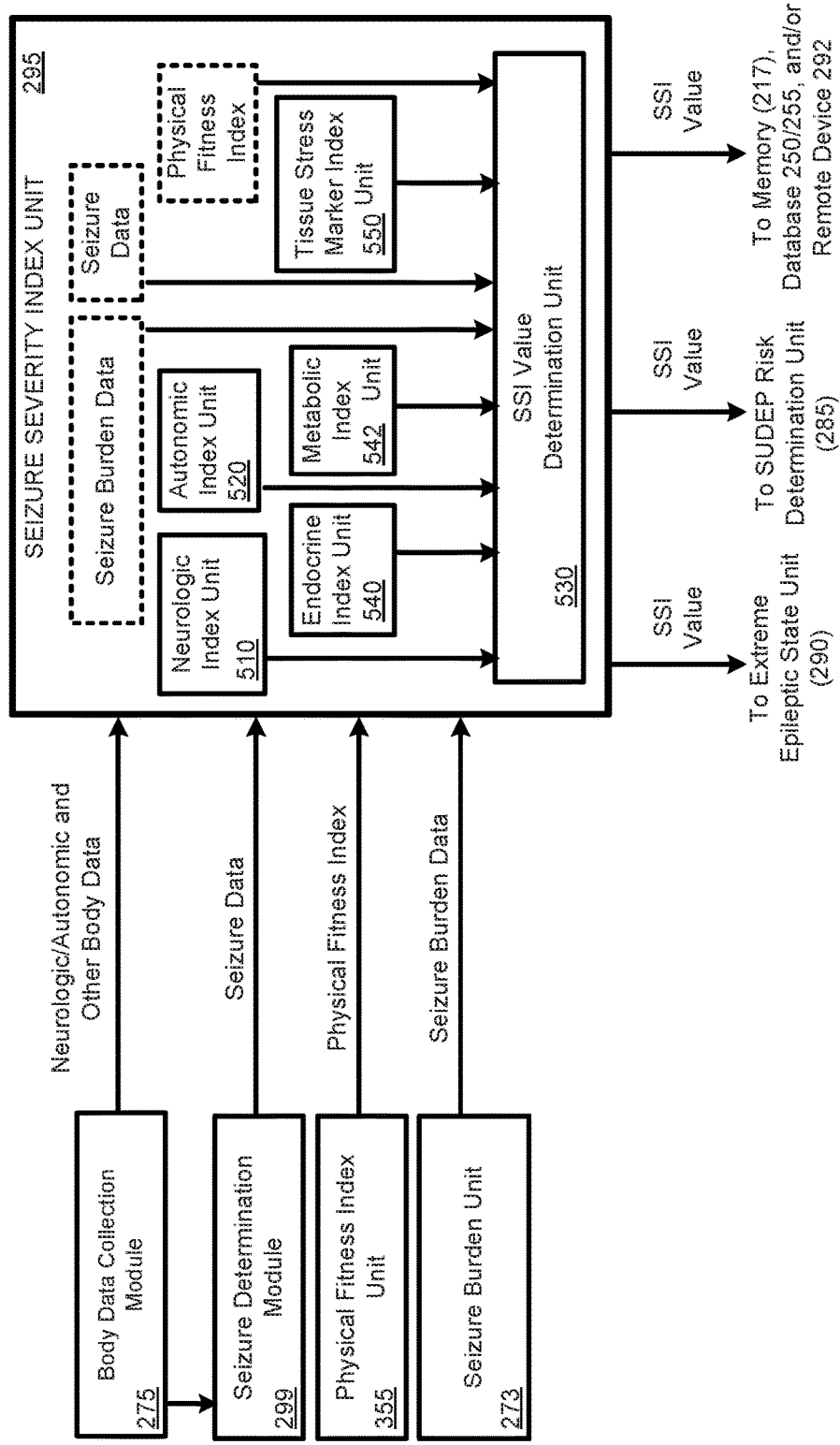
FIG. 5A provides a stylized diagram of a seizure severity index unit for determining a seizure severity index using body data and seizure data, in accordance with one illustrative embodiment of the present invention.

Turning now to FIG. 5A, a block diagram depiction of a seizure severity index unit 295 (SSI unit) is provided, in accordance with one illustrative embodiment of the present invention. In one embodiment, the SSI unit 295 may be adapted to determine a seizure severity index (SSI). The SSI unit 295 may use body data and/or seizure data (e.g., seizure intensity data, seizure duration data and/or seizure spread data) in determining the SSI. In one embodiment, body data collection module 275 may send body data to SSI unit 295. In one embodiment, the SSI unit 295 may include at least one of a neurologic index unit 510, an autonomic index unit 520, an endocrine index unit 540, a metabolic index unit 542 and/or a stress marker index unit 550 and/or a physical fitness/integrity index unit 555. The neurologic index unit 510 may be adapted to determine a neurologic index value using neurologic body data from the body data collection module 275. The autonomic index unit 520 may be adapted to determine an autonomic index value using autonomic body data from the body data collection module 275. The endocrine index unit 540 may be adapted to determine an endocrine index value using body data from the body data collection module 275. The metabolic index unit 542 may be adapted to determine a metabolic index value using body data from the body data collection module 275. The stress marker index unit 550 may be adapted to determine a stress marker index value using body data from the body data collection module 275. The physical fitness/integrity index unit 555 may be adapted to determine a stress marker index value using body data from the body data collection module 275. It is noted that the seizure determination module 299 may send seizure data to the SSI unit 295 and that units 510, 520, 540, 542, 550 and 555 may be adapted to determine their respective indices based on seizure data from seizure determination module 299.

The neurologic index unit 510, autonomic index unit 520, endocrine index unit 540, metabolic index unit 542, stress marker index unit 550, and physical fitness/integrity unit 555 may be adapted to transmit their respective index values to an SSI value determination unit 530. The SSI value determination unit 530 may use a neurologic index value, an autonomic index value, an endocrine index value, a metabolic index value, a stress marker index value, a physical fitness/integrity index determined by the seizure data, and/or other body data to determine a seizure severity index value (SSI value), as described above with respect to FIG. 2. The SSI value may be transmitted/provided to the extreme epileptic event/state detection, quantification and risk determination unit 290, the warning unit 289, the seizure (extreme seizure) ranking unit 247, a memory 217, a database 250/255, a remote device 292, and/or other components of the MD 200. It is noted that in some embodiments the SSI value may be sent directly to the warning unit 289 and/or the seizure (extreme seizure) ranking unit 247 without being sent to the extreme epileptic event/state detection, quantification and risk determination unit 290.

Figure 5B:
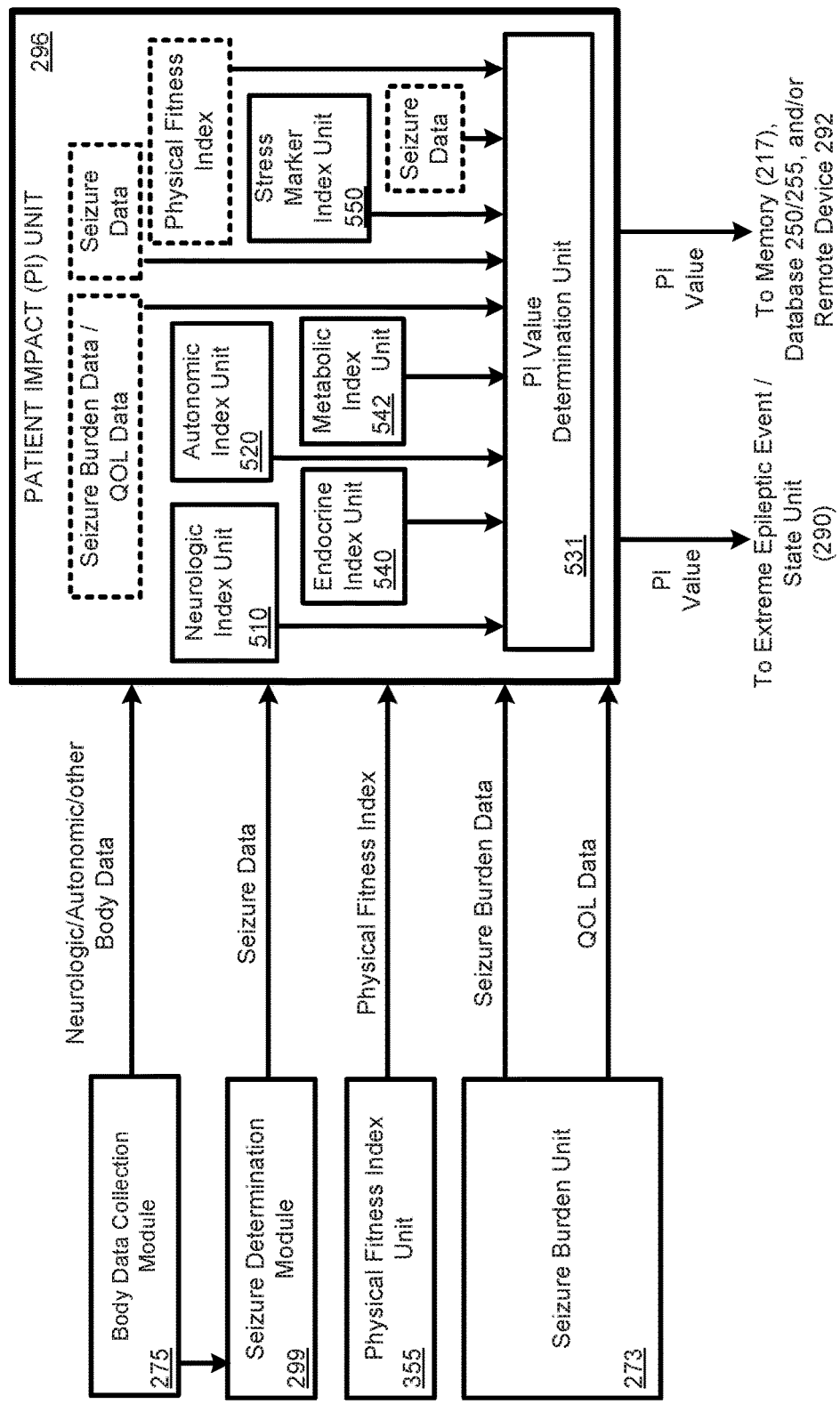
FIG. 5B provides a stylized diagram of a patient impact unit for determining a patient impact using body data and seizure data, in accordance with one illustrative embodiment of the present invention.

Turning now to FIG. 5B, a block diagram depiction of a patient impact unit 296 is provided, in accordance with one illustrative embodiment of the present invention. In one embodiment, the PSimp unit 296 may be adapted to include a seizure severity index (SSI) unit 295 or to use the data from a separate SSI unit 295. The PSimp unit 296 or the PSB unit 273 may receive data from the physical fitness/integrity index unit 555. In one embodiment, body data collection module 275 may send body data to PSimp unit 296. Such body data may include, but is not limited to, neurologic and/or autonomic body data, endocrine data, stress marker data, physical activity data, and/or the like. Likewise, the seizure determination module 299 may send corresponding data to the PSimp unit 296. The PSimp unit 296 may, in one embodiment, comprise a QOL index unit 544. The QOL index unit 544 may provide a QOL index value for use in a PSimp determination, in accordance with one embodiment, or in other embodiments, the QOL index may be computed separately from the PSimp value. The PSimp value determination unit 531 may use seizure burden data, QOL data and/or other body data to determine a patient seizure impact value (PSimp value). The PSimp value may be transmitted/provided to the extreme epileptic event/state detection, quantification and risk determination unit 290, the warning unit 289, a memory (217), a database 250/255, a remote device 292, and/or other components of the MD 200.

Figure 5C:
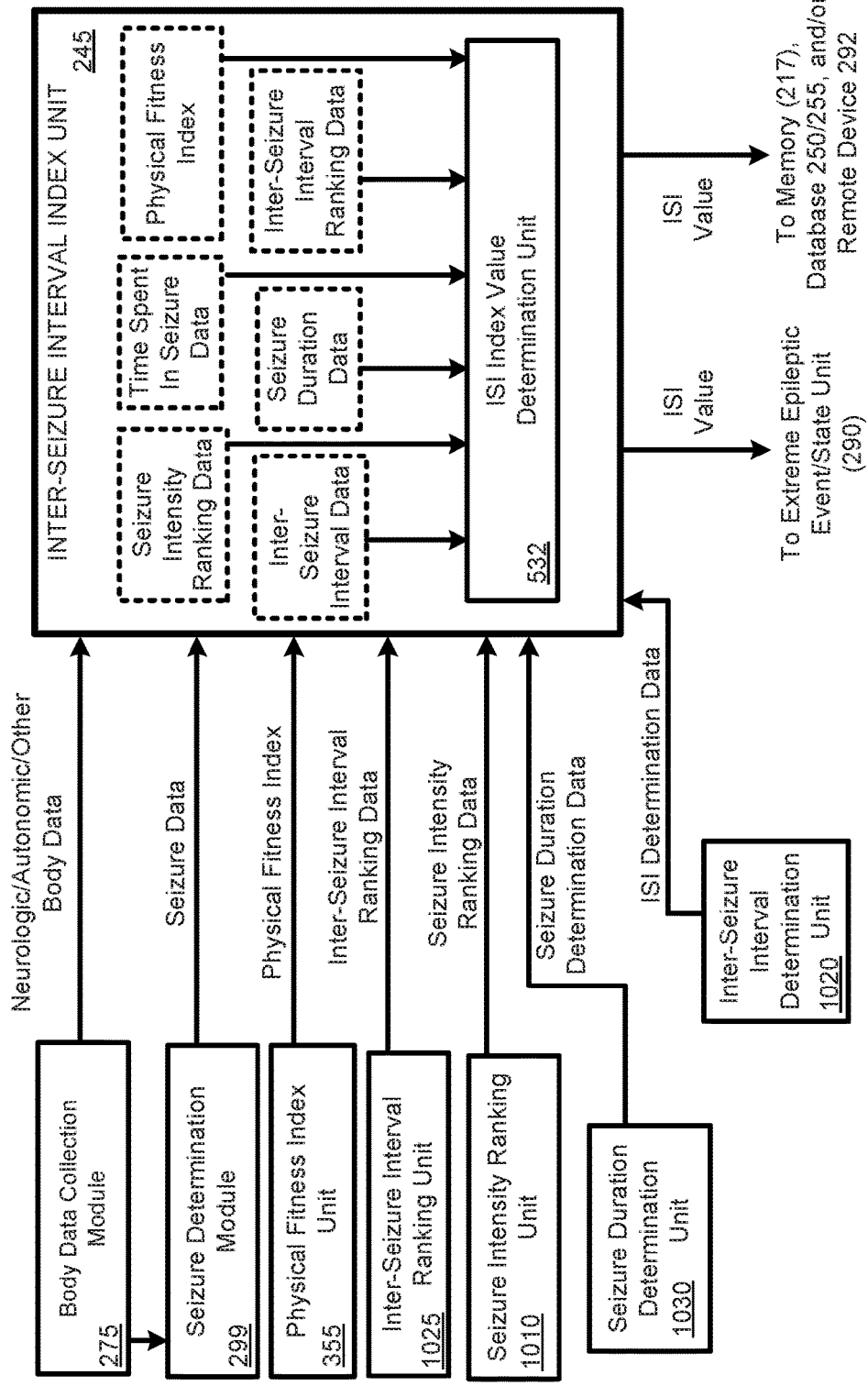
FIG. 5C provides a stylized diagram of an inter-seizure interval index unit for determining a time elapsed between the onset of consecutive seizures using body data, in accordance with one illustrative embodiment of the present invention.

Turning now to FIG. 5C, a block diagram depiction of an inter-seizure interval index unit 245 (ISI index unit) is provided, in accordance with one illustrative embodiment of the present invention. In one embodiment, the ISI index value determination unit 532 may use a neurologic index value, an autonomic index value, an endocrine index value, a stress marker index value, seizure data and/or other body data to determine an inter-seizure interval index value (ISI index value), as described above with respect to FIG. 2. In one embodiment, the ISI index value may be indicative of extreme seizure events/states if the time interval between two or more seizures is below (by one or more standard deviations) the mean of a normalized distribution of ISIs or at or below the $20^{th}$ percentile of distribution values. The ISI index value may be transmitted/provided to the extreme epileptic event/state detection, quantification and risk determination unit 290, the warning unit 289, the inter-seizure interval ranking unit 1025, a memory (217), a database 250/255, a remote device 292, and/or other components of the MD 200. It is noted that in some embodiments the ISI value may be sent directly to the warning unit 289 and/or the seizure (extreme seizure) ranking unit 247 without being sent to the extreme epileptic event/state detection, quantification and risk determination unit 290.

In one embodiment, the ISI index unit 245 may be adapted to determine an inter-seizure interval (ISI). The ISI index unit 245 may use the time of onset and/or termination of at least two consecutive or non-consecutive seizures from a seizure spread, duration and intensity determination unit 294 to calculate the time elapsed between the seizures. In one embodiment, the ISI index unit 245 may receive data from duration determination unit 1030 (see FIG. 11 below) and inter-seizure interval data from an inter-seizure interval determination unit 1020 (see FIG. 11 below), body data from the body data collection module 275 and/or other seizure data (not shown) in determining the ISI index. In one embodiment, body data collection module 275 may send body data to the ISI index unit 245. Such body data may include, but is not limited to, neurologic and/or autonomic body data, endocrine data, stress marker data, physical activity data, and/or the like. Likewise, the seizure determination module 299 may send seizure data to the ISI index unit 245.

Figure 6:
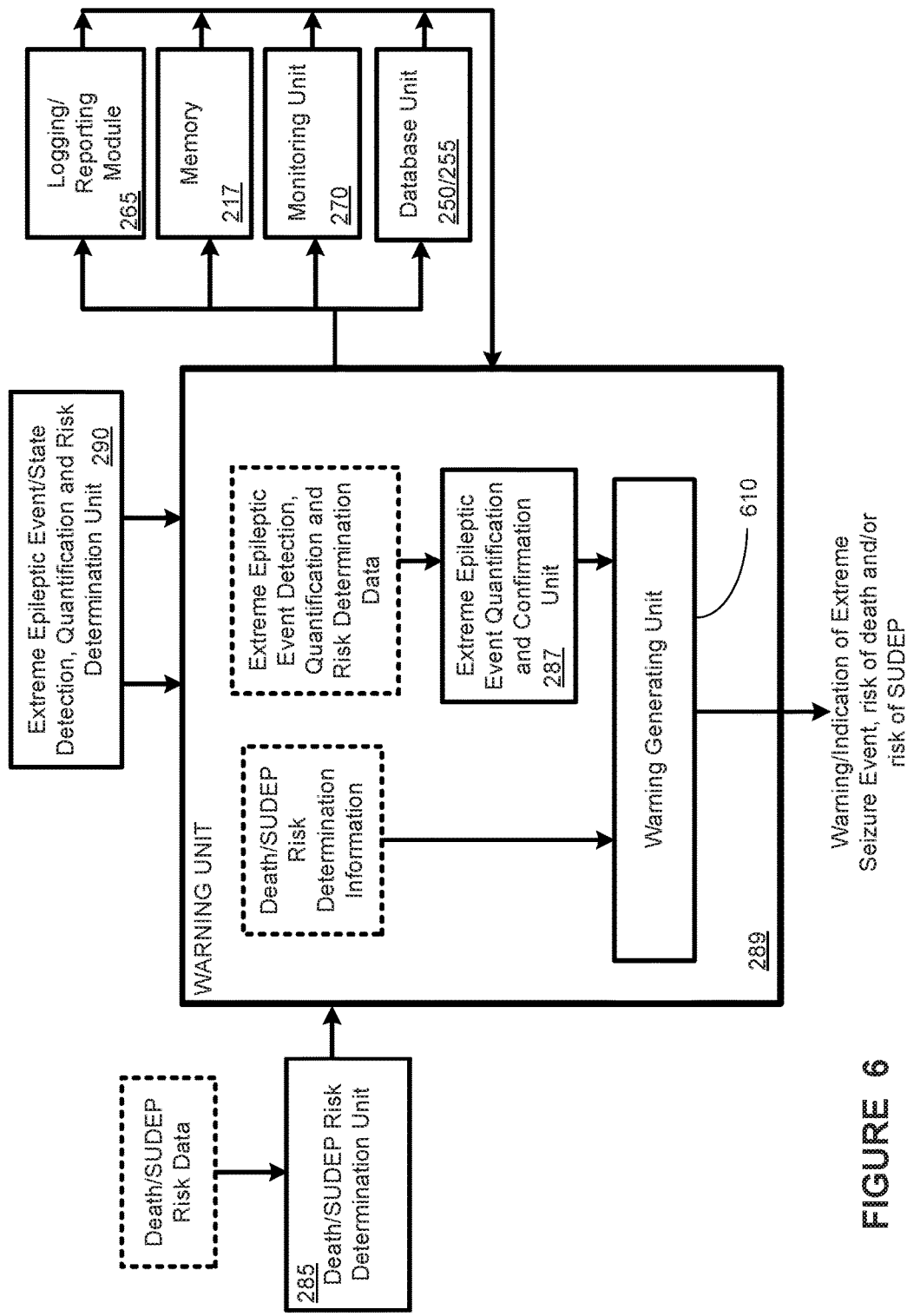
FIG. 6 provides a stylized diagram of a warning unit for warning of a patient's increased risk of death or of the risk occurrence, in accordance with one illustrative embodiment of the present invention.

Turning now to FIG. 6, a block diagram depiction of a warning unit 289 is provided, in accordance with one illustrative embodiment of the present invention. In one embodiment, the warning unit 289 may be adapted to provide a warning of a seizure, seizure events and/or extreme seizure events. In various embodiments, extreme seizure events may include a present or past state of status epilepticus, an increased risk of status epilepticus, a risk of SUDEP associated with a seizure, an increased risk of SUDEP associated with a seizure, the occurrence of injury or of an increased risk of injury and/or the like. The warning unit 289 may provide a warning to a patient, a physician, a caregiver, the logging/reporting module 265, the monitoring unit 270, the remote device 292, the memory 217, the database 250/255, and/or the like.

The warning unit 289 may include a warning generating unit 610, in accordance with one embodiment. The warning unit 289 may be adapted to receive SSI data from the SSI Unit 295, ISI data from the ISI Index Unit 245, PISI data from the (post-ictal determination unit 1033), physical fitness/physical integrity data from the physical fitness/integrity index unit 555, PSimp data from the PSimp unit 296, extreme epileptic event/state data from extreme epileptic event/state detection, quantification and risk determination unit 290, and/or extreme seizure event confirmation data from extreme epileptic event confirmation unit 287. In various embodiments, the warning unit 289 may be adapted to receive other signals and/or data in addition to, or alternatively to, the aforementioned data, as shown in FIG. 6. In one embodiment, the warning generating unit 610 may take any data received by the warning unit 289 as an input to generate a warning. The warning may be a general warning related to a seizure or extreme seizure event or state such as status epilepticus, an upgrade in warning of an existing extreme seizure state/event, or related to an injury associated with a seizure (e.g., which prolongs the time the patient is immobile or in the recumbent position beyond a mean, median or percentile time for that patient). In one embodiment, the warning unit 289 may include an extreme epileptic event confirmation unit 287. The extreme epileptic event confirmation unit 287 may take data from the extreme epileptic event/state detection, quantification and risk determination unit 290 and confirm or verify that an extreme epileptic event/state is likely, is about to occur, is occurring or has occurred. If the extreme event/state is confirmed by the extreme epileptic event/state determination unit 287, the confirmation may be sent to the warning generating unit 610, and the warning may proceed. If the extreme event/state is not confirmed by the extreme epileptic event/state determination unit 287, the warning may be blocked or disabled, and data associated with the blocked/disabled warning may be removed from the logging/reporting module 265, the monitoring unit 270, the remote device 292, the memory 217, the database 250/255, and/or the like.

Warnings may include sounds or lights, automated emails, text messages, telephone calls, or video messages sent from the MD 200, either directly or via a monitoring unit 270, to the police, an EMT unit, the patient's physician/caregiver's cellular telephone, PDA, computer 150, television, etc. Such warning(s) may allow the patient and/or caregivers to take measures protective of the patient's well-being and those of others, e.g., pulling out of traffic and turning off a car, when the patient is driving; stopping the use of machinery, contacting another adult if the patient is providing childcare, removing the patient from a swimming pool or bathtub, lying down or sitting if the patient is standing, etc. The warning may, when appropriate, automatically disable operation of a vehicle or of power equipment or inflate a life saver (e.g., for a patient who is swimming) or bags placed on the chest or back of a patient to minimize risk of injury in case of falls.

Figure 7:
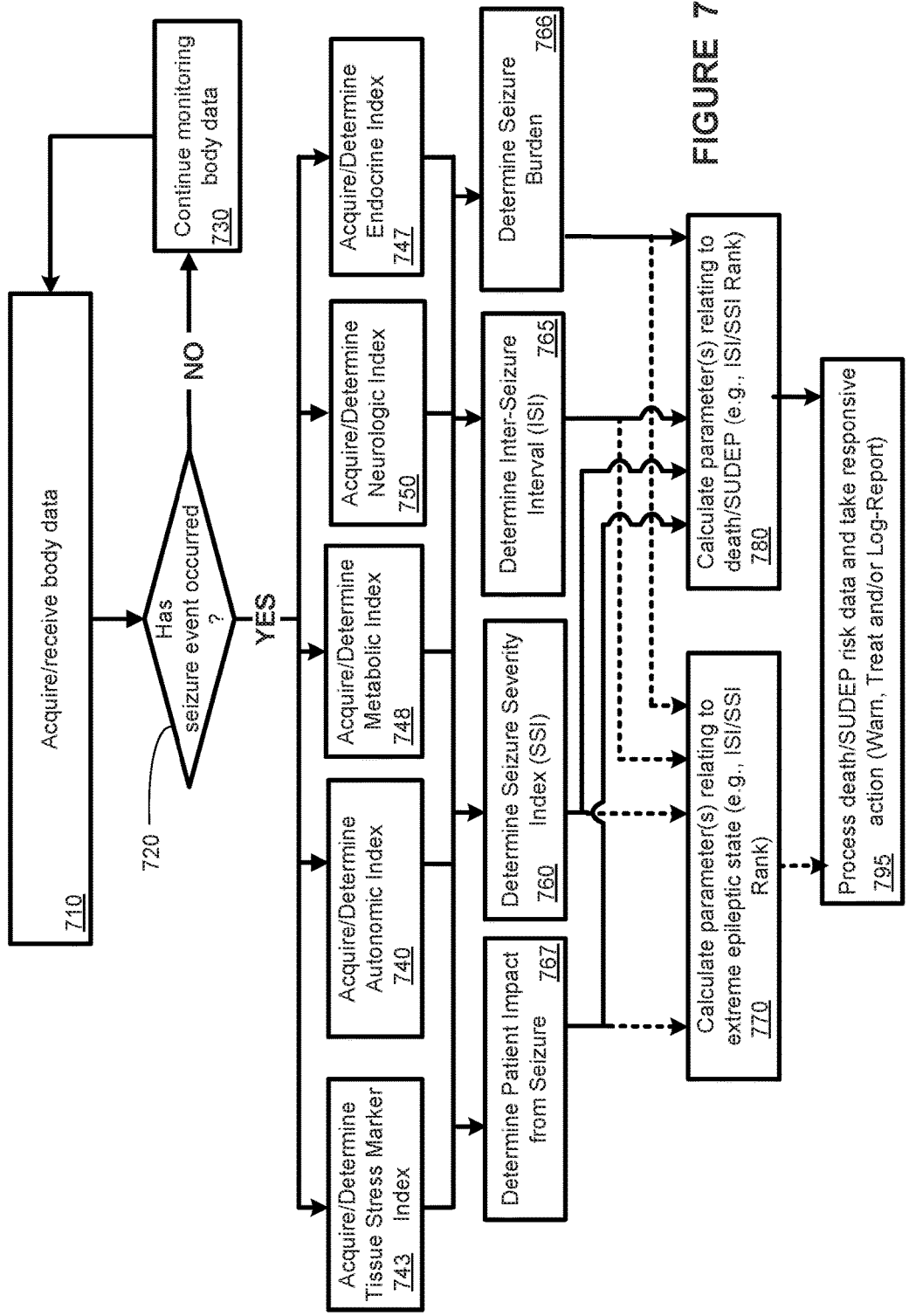
FIG. 7 provides a flowchart depiction of a method for identifying and/or managing an increased risk of death, in accordance with one illustrative embodiment of the present invention.

Turning now to FIG. 7, a flowchart depiction of a method for taking action (e.g., warning, providing treatment/therapy, logging, etc.) in response to the occurrence of a seizure event and/or an extreme seizure event is provided, in accordance with one illustrative embodiment of the present invention. The MD acquires and/or receives body data at step 710, typically from the body data collection unit 275 which buffers, amplifies/conditions and performs A/D conversion of the body data. Using data from unit 275, the seizure determination module 299 in the MD 200 determines, through operations including but not limited to calculations based on at least one index, if a seizure event has occurred, is likely to occur or is occurring (step 720). If the MD 200 determines that no seizure or seizure event has occurred, the IMD 200 will continue to monitor for body data (step 730; return the flow to step 710).

If the medical device determines (at step 720) that a seizure event has occurred or is occurring or is likely to occur, based on at least one of an autonomic index, a neurologic index, a stress marker index, a metabolic index and/or an endocrine index (e.g., using an SSI unit 295, an ISI index unit 245, a PSimp unit 296 and/or another unit/module in the MD 200), the subsequent step 740 may be to determine, e.g., using unit 290, if the event is extreme. Determination that the event is extreme, may trigger responsive actions (step 750) including but not limited to delivering a therapy or therapies, (unit 220), warning(s) (unit 289) and requesting confirmation via unit 287 that the event is extreme (step 755), and if it is deemed extreme, it may be then ranked (step 760), typically using unit 247. If the event is not confirmed as extreme, all responsive actions may be terminated (step 770). At any given step, information yielded by that step, and the decisions made based on this information, may be send to logging/reporting unit 265 (step 745) and/or to memory 217. Steps 750, 760 and 770 may begin at the same time and end at the same time (or at different times) according to various embodiments. Further, it is contemplated that events may be logged after a determination and/or confirmation of an extreme event (steps 740/755) has occurred.

The number of steps and the order in which they are adopted may vary according to one of several possible embodiment contemplated herein. For example, confirmation that the event is extreme may be unnecessary if all indices (autonomic, neurologic, endocrine, metabolic, tissue stress marker, physical integrity, etc.) are determined simultaneously. However, if all indices are not measured, those untested may be determined in any number and/or temporal sequence for the purpose of confirmation. The medical device 200 may determine an SSI value using at least one of an autonomic index, a neurologic index, a stress marker index, a metabolic index and/or an endocrine index; the medical device 200 may determine an inter-seizure interval index (ISI index) value using at least one of an autonomic index, a neurologic index, a stress marker index, a metabolic index and/or an endocrine index; the medical device 200 may determine a physical fitness/integrity index value using at least one of an autonomic index, a neurologic index, a stress marker index, a metabolic index and/or an endocrine index. Typically, the SSI value is determined by SSI unit 295 (which may comprise an SSI determination unit (530)). Typically, the ISI index value is determined by ISI index unit 245. Typically, the physical fitness/integrity index value is determined by physical fitness/integrity index unit 355. In one or more embodiments, additional data may also be used to determine the ISI index value and/or physical fitness/integrity index value. Depending upon the embodiment, one or more of the SSI value, the ISI index value and/or the physical fitness/integrity index value may be determined. For example, in one embodiment, only the SSI value may be calculated while the ISI index value is not calculated. In another embodiment, only the ISI index value may be calculated while the SSI value is not calculated. In one or more embodiments, additional data may also be used to determine the SSI values, ISI values and/or physical fitness/integrity index values.

The confirmation of an extreme epileptic event/state parameter(s) may be performed by an extreme epileptic event/state confirmation unit 287 (at step 755). The confirmation of an extreme epileptic event/state may be based upon one or more SSI values and/or one or more ISI index values as described above, and/or be based upon other data/indices as described above. From step 755, the flow may proceed to determining a patient seizure impact (PSimp) value (step 780), and in some embodiments, the flow may then proceed to determining a seizure burden value (step 790). The medical device 200 may determine a PSimp value using at least one of an autonomic index, a neurologic index, a stress marker index, a metabolic index and/or an endocrine index, a quality of life index or a physical fitness/integrity index and or the like (step 780). The medical device 200 may determine a seizure burden value using at least one of an autonomic index, a neurologic index, a stress marker index, a metabolic index and/or an endocrine index and/or the like (step 790). Other procedures/modules may be used to determine a seizure burden and/or patient seizure impact. For example, an Acquire/Determine Physical Fitness Index/Body Integrity Unit (not shown) may use these data to determine seizure burden and/or patient seizure impact. The MD 200 may also take responsive action for extreme epileptic event/state (at step 750) that may include, but is not limited to, drug/chemical therapy, electric stimulation, cooling, supportive care, oxygen administration, warning, logging/reporting, and/or the like. It is also contemplated that a patient's physical activity may be stored in a memory 217 or logged/reported in one or more of the database 250/255 and the remote device 292.

Risk of death confirmation may be based on assessment/determination of arousal and/or the presence or absence of other indicia indicative of organ dysfunction. In one embodiment, only one of these may be used to confirm a risk of death. For example, if the patient is not arousable and all other indicia indicative of organ dysfunction are absent, the risk may be confirmed, or if other indicia are present and the patient is arousable, the risk may be also confirmed. In another embodiment, both impaired arousal and presence of indicia indicative of organ dysfunction are required to confirm the risk of death In the case that both are required, and only one is abnormal, monitoring of arousal and other indicia may continue until the risk is confirmed or not confirmed. In either case, actions to treat the patient and warn may be taken until a confirmation is confirmed or rejected.

Figure 8A:
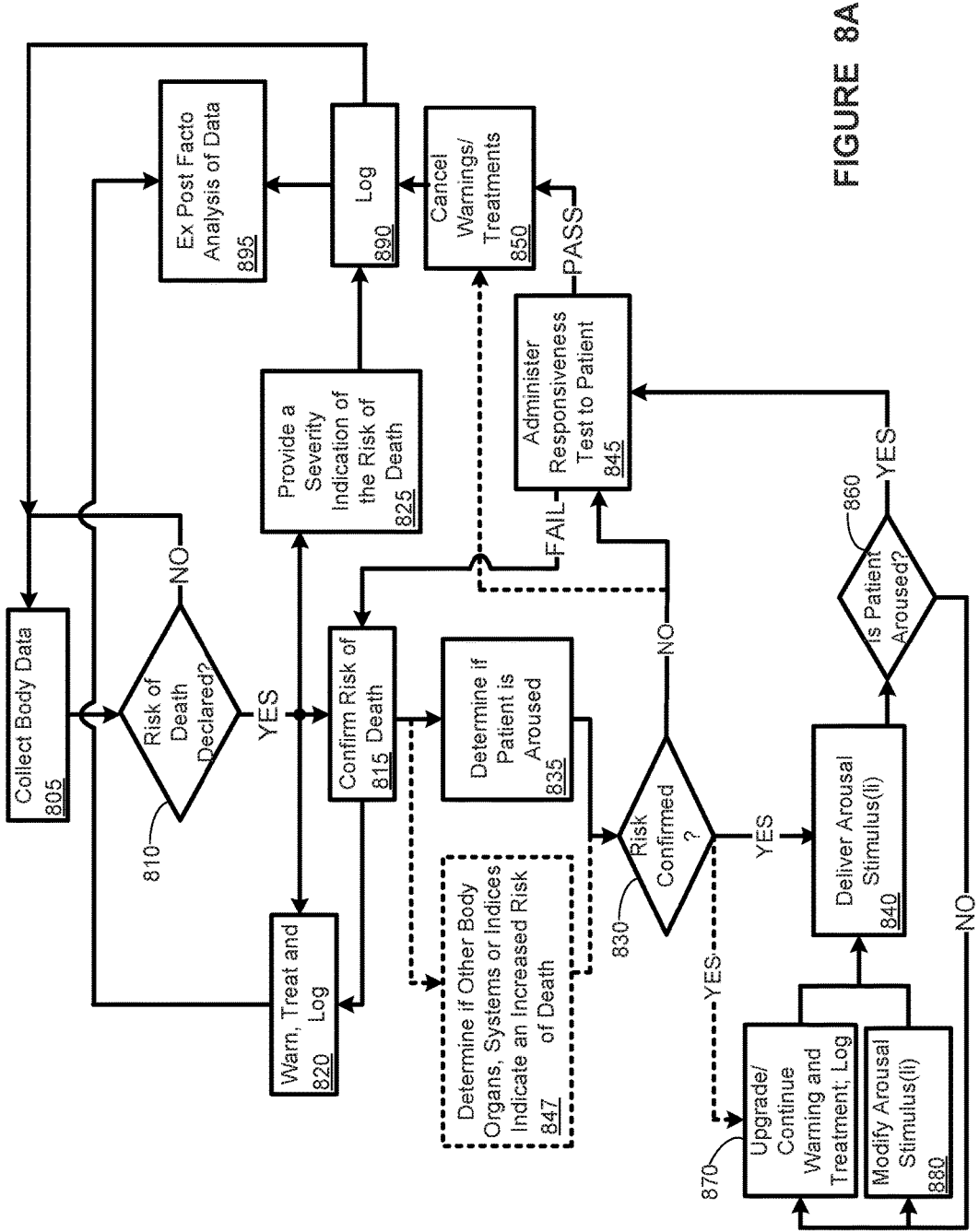
FIG. 8A provides a flowchart depiction of a method implementing responsive actions (warning, treatment, data logging among others) in response to declaration of and confirmation that there is an increased risk of death, in accordance with one illustrative embodiment of the present invention.

Turning now to FIG. 8A, a flowchart depiction of a method implementing responsive actions (e.g., warning, treatment, and data logging among others) in response to determining that there is a furthered increased risk of death, in accordance with one illustrative embodiment of the present invention, is depicted. The MD 200 may collect body data (as described elsewhere herein) (step 805) and based upon the collected body data, the MD 200 may declare that a patient may have a further increase in risk of death (step 810). It should be noted that in some embodiments a risk of death may be based on an extreme epileptic event (i.e., the occurrence of an actual extreme epileptic seizure or condition), while in other embodiments the elevated risk of death may be due to a patient's level and type of activity (e.g., swimming), a patient's condition (e.g., patient has the flu) or the patient's environment (e.g., the swimming pool is deep and the patients is alone). If the MD 200 determines a patient does not have a risk of death, a risk of death may not be declared (step 810), and the flow may return to step 805 where the MD 200 may proceed to collect body data. If the MD 200 determines a patient has a risk of death, the MD 200 may declare a risk of death (step 810), and the flow may in some embodiments proceed to one, some, or all of the following steps: a risk of death confirmation (step 815), warning of, treating and/or logging the risk of death (e.g., logging in a memory device 217 or database 250/255) (step 820) and/or providing a severity indication of the risk of death (step 825). It should be noted that these steps may be performed in any order, sequentially, in parallel or some combination thereof. In one embodiment, the MD 200 may delay warning and/or treating the patient until the risk of death is confirmed (step 830).

From step 820, the flow may proceed to performing an ex post facto analysis of some or all of the logged data acquired in step 820 (at step 895). From step 825, the flow may proceed to step 890 where the severity indication of the risk of death (provided in step 825) may be logged (e.g., in a memory device 217 or database 250/255) and may then proceed to step 895 to perform an ex post facto analysis of some or all of the logged data acquired in step 890. From step 890 the flow may proceed back to step 805 and collect body data.

From step 815, the flow may proceed to step 820 (warning, treating and logging, as described above) and/or to confirming the risk of death (at steps 835 and/or 847). The flow may proceed from step 815 to steps 820, 835 and/or 847 in any order, sequentially, in parallel or some combination thereof. At step 835, it may be determined if the patient is aroused or arousable. At step 847 it is determined if other body organs/systems' indices also indicate an increased risk of death for the patient. It should be noted that in some embodiments, only step 835 may be performed. In other embodiments, both steps 835 and 847 or only step 847 may be performed to confirm a risk of death for the patient. At step 830, if the risk of death is not confirmed, the flow may proceed, in accordance with an embodiments, to one or both of: a) step 845 to administer a responsiveness test to the patient as an added precaution and/or b) to step 850 to cancel some, any and/or all of the warnings and/or treatments provided at step 820. In one embodiment, a risk of death may be not confirmed if a patient is aroused and other indicia of an increased risk of death are absent and in another embodiment, only one of these two need be impaired to confirm the increased risk of death.

From step 850, the flow may proceed to step 890, as described above. If, at step 830, the risk of death is confirmed, the flow may proceed to one, some or all of steps 840, 845 and/or 870). It should be noted that in some embodiments if step 847 is not performed, the flow may not proceed from step 830 to step 870. If the patient is aroused/arousable and other indicia of an increased risk of death are not present/detected, the flow may proceed to administer a responsiveness test to the patient (step 845). If the patient is not aroused/arousable, the flow may proceed to deliver one or more arousal stimuli to the patient (step 840). The one or more arousal stimuli may be any of those described herein, or other stimuli as would be known by one of ordinary skill in the art having the benefit of this disclosure. If a determination of an increased risk of death is made in step 847 (i.e., based upon other body organs, systems and/or indices), the flow may proceed to upgrade/continue any or all treatments and/or warnings, as well as log any related information (step 870). It should be noted that in some embodiments, the flow may proceed from step 830 directly to step 870 whether or not the patient is aroused (as determined in step 835).

From step 840, the flow may proceed to determining if the patient is now aroused/arousable (step 860). If the patient is aroused/arousable, the flow may proceed to administer a responsiveness test to the patient (step 845). If the patient is not aroused/arousable, the flow may proceed to upgrade and/or continue treatment(s) and/or warning(s) as well as log information related to the status of the patient and information related to the upgrade/continuation of treatment(s) and/or warning(s) (step 870). The flow may also proceed from step 860 to modify some or all of any arousal stimuli (at step 880). Arousal stimuli may be modified by adding/removing stimuli, changing stimuli (e.g., in strength, intensity and/or amount, progressing hierarchically to other stimuli, and/or the like, as described herein. Steps 870 and 880 may be performed sequentially or in parallel. From steps 870 and 880, the flow may proceed back to step 840 where the one or more arousal stimuli are delivered to the patient.

At step 845 (if the patient is aroused/arousable from steps 835 (via step 830) and/or 860), a responsiveness test may be administered to the patient. Responsiveness tests to be administered may be any of those described herein, or other tests as would be known by one of ordinary skill in the art having the benefit of this disclosure. If the patient does not take the test or fails the test, the flow may proceed back to determining a risk of death for the patient (at step 815) and executing the steps described in FIG. 8. If the patient passes the responsiveness test, the flow may proceed to cancel warnings/treatments as described above (step 850).

In one embodiment, determining other body organ indices for indicia of an increased risk of death (step 847) may include, but is not limited to, determining indices of a certain class or subclass of indices. For example, the class of autonomic indices may include cardiac, respiratory, skin resistivity and pupillary reflex indices. In determining indices indicative of an increased risk of death, in accordance with one embodiment, one or more autonomic indices may be determined. Similarly, neurologic indices such as kinetic, responsiveness and/or awareness indices may be determined. It is contemplated that metabolic, endocrine, tissue stress and/or physical fitness/integrity indices may be grouped/classified and determined in a similar fashion. Subclasses may also be used for determining indices indicative of an increased risk of death. Examples of subclasses of indices include, but are not limited to: cardiac indices such as heart rate, EKG morphology, hearth rhythm, PKG and/or the like; respiratory indices such as oxygen saturation, respiration rate, respiration rhythm(s), respiration pattern(s), tidal volume and/or the like; kinetic indices such as tone (EMG), body posture, body and/or body part position(s), movement direction, movement speed, movement acceleration and/or the like; tissue stress marker indices such as troponin, lactic acid and/or the like.

Figure 8B:
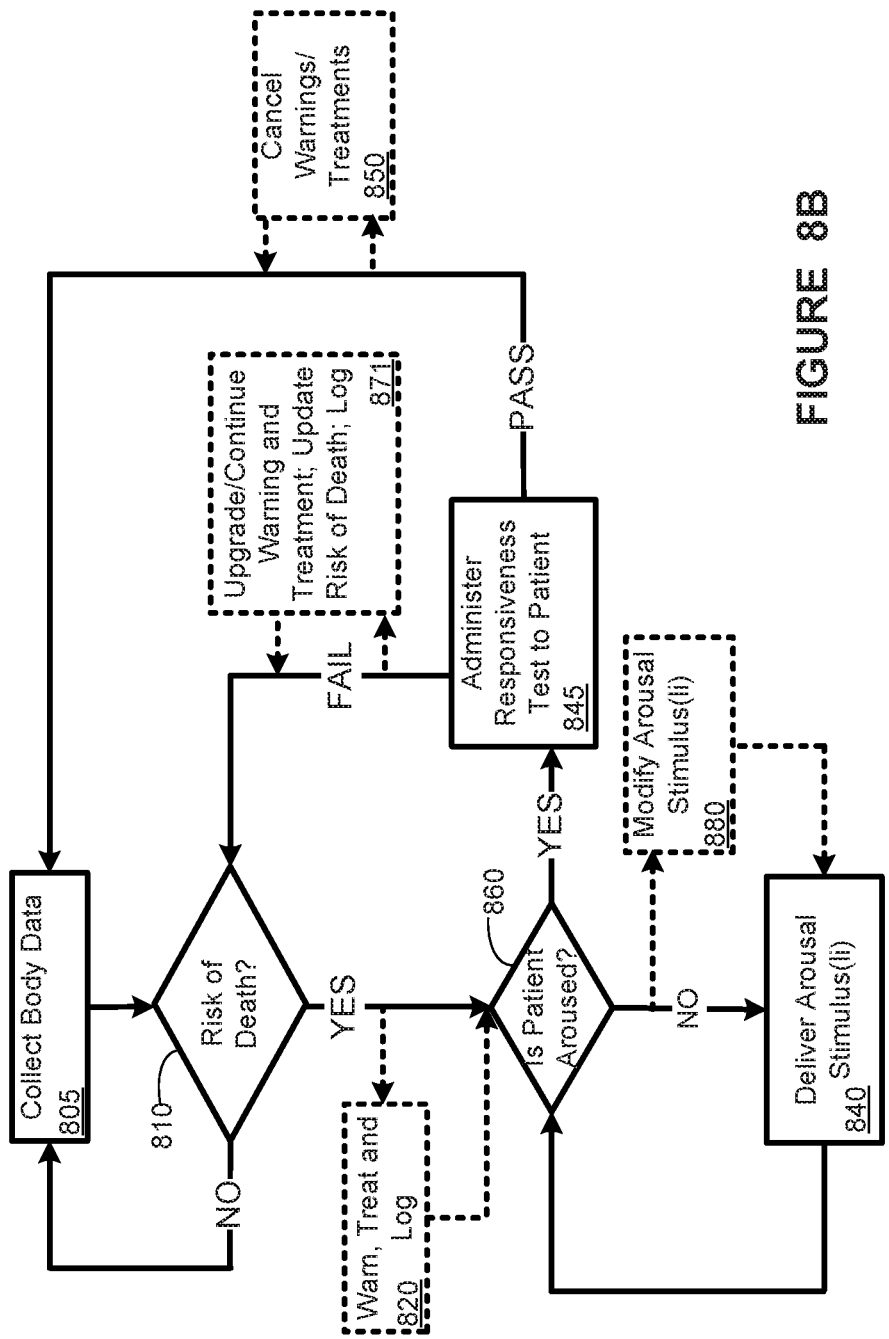
FIG. 8B provides a more focused flowchart depiction of the method for implementing responsive actions (warning, treatment, data logging among others), depicted in FIG. 8A, in response to determining that there is an increased risk of death, in accordance with one illustrative embodiment of the present invention.

FIG. 8B is a zoomed-in flowchart depiction of FIG. 8A, focusing on a method for implementing responsive actions (e.g., warning, treatment, and data logging among others) in response to determining that there is an increased risk of death, in accordance with one illustrative embodiment of the present invention. The MD 200 may collect body data (as described elsewhere herein) (step 805) and based upon the collected body data, the MD 200 may determine that a patient may have an increased risk of death (step 810). If the MD 200 determines a patient does not have a risk of death (step 810), the flow may return to step 805 where the MD 200 may proceed to collect body data. If the MD 200 determines a patient has a risk of death (step 810), the MD 200 may declare a risk of death (step 810), and the flow may in some embodiments proceed to one or both of the following steps: determining if the patient is aroused (step 860), warning of, treating and/or logging the risk of death (e.g., logging in a memory device 217 or database 250/255) (step 820). It should be noted that these steps may be performed in any order, sequentially, in parallel or some combination thereof.

From step 860, if the patient is aroused/arousable, the flow may proceed to administer a responsiveness test to the patient (step 845). If the patient is not aroused/arousable, the flow may proceed to deliver one or more arousal stimuli to the patient (step 840). The one or more arousal stimuli may be any of those described herein, or other stimuli as would be known by one of ordinary skill in the art having the benefit of this disclosure. In one embodiment, the flow may proceed from step 860 to modify some or all of any arousal stimuli (at step 880) before proceeding to step 840. For example, on subsequent patient arousal determinations (step 860), one or more arousal stimuli may be upgraded or otherwise modified. Arousal stimuli may be modified by adding/removing stimuli, changing stimuli (e.g., in strength, intensity and/or amount, progressing hierarchically to other stimuli, and/or the like, as described herein. From step 840, the flow may proceed back to step 860 to determine if the patient is aroused.

At step 845 (if the patient is aroused/arousable from step 860, a responsiveness test may be administered to the patient. Responsiveness tests to be administered may be any of those described herein, or other tests as would be known by one of ordinary skill in the art having the benefit of this disclosure. If the patient does not take the test or fails the test, the flow may proceed back to determining a risk of death for the patient (at step 810). In one embodiment, the flow may proceed to step 871 before proceeding to step 810. At step 871 the flow may proceed to upgrade/continue any or all treatments and/or warnings, update the risk of death and/or log any related information. If the patient passes the responsiveness test, the flow may proceed back to step 805 to collect body data. In one embodiment, the flow may proceed to step 850 to cancel any or all warnings and treatments before proceeding back to step 805.

Figure 9:
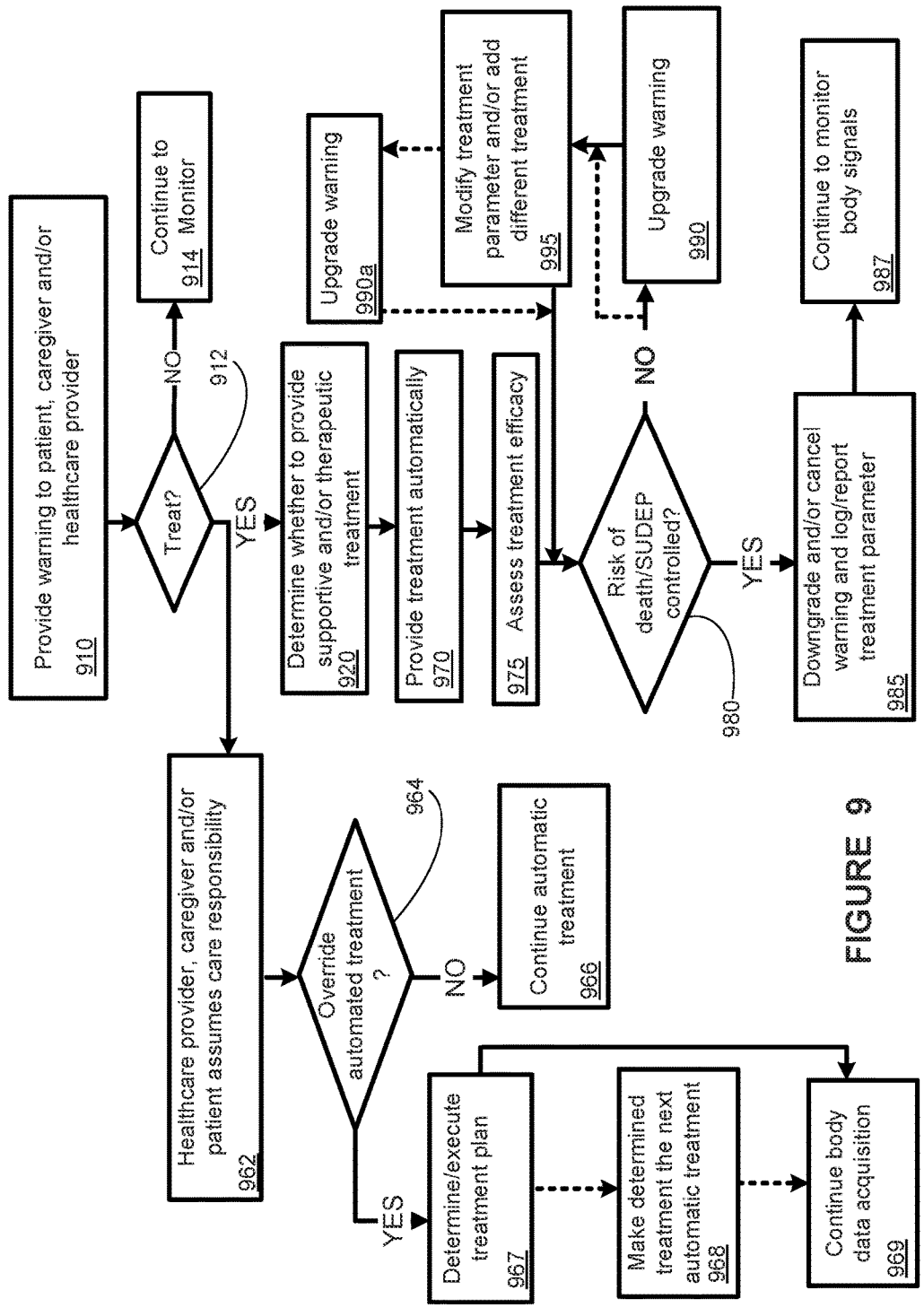
FIG. 9 provides a flowchart depiction of a method for warning and/or providing a treatment to a patient with an increased risk of death, in accordance with one illustrative embodiment of the present invention.

Turning now to FIG. 9, a flowchart depiction of a method for warning and/or providing a treatment to a patient in response to an extreme seizure event is provided, in accordance with one illustrative embodiment. The MD 200 may provide a warning of a state of an extreme epileptic event/state via the warning unit 289 in one or more embodiments (step 910). The warning may be to a patient, a physician, a caregiver, emergency response personnel, a logging/reporting module 265, a monitoring unit 270, a remote device 292, an external entity 265 and/or the like. The warning may indicate an extreme epileptic event/state (e.g., a severe seizure, status epilepticus, or an injury resulting from an otherwise non-extreme seizure). At step 912, the decision is made whether or not to treat the patient based upon the warning from step 910. If it is determined that no treatment will be performed, the flow proceeds to step 914 where patient monitoring and body data acquisition continues. If it is determined that treatment will be administered, the flow may proceed to one or both of steps 920 and/or 962.

A determination may be made as to which treatment modality(ies) are to be provided to a patient (step 920). Modalities include, but are not limited to, electrical currents, chemical/drug therapies and/or supportive treatments such as cooling, fluids, pressor agents and/or oxygen. In one embodiment, the MD 200 may automatically implement a predetermined treatment to reduce the risk of an extreme epileptic event/state and/or to reduce the effects of a state of an extreme epileptic event/state in the patient (step 970) using one or more treatment modalities. In reference to supportive care, seizures are powerful biological stressors and inductors of stress markers and may deplete the body of certain anti-oxidants such as glutathione peroxidase. The concentration of certain compounds that protect from biological stress (e.g., dehydroepiandrosterone or its sulfate conjugate, glutathione peroxidase and/or the like) or the body's total antioxidant capacity may be measured to determine if it is adequate, and if not, to increase it using available antioxidants to preserve the integrity of organs/functions so as to stall disease progression. Stress marker index indices and antioxidants may be measured in brain (invasively and/or non-invasively), CSF, plasma, serum, erythrocytes, urine, and saliva (e.g., alpha amylase).

Upon delivery of automatic treatment(s), an assessment of the efficacy of the treatment may be performed (step 975) in some embodiments. Based upon the assessment of the efficacy of treatment, a determination is made whether the state of the extreme epileptic event/state is at least substantially controlled (step 980). If a determination is made that the extreme epileptic event/state is not substantially controlled (step 980), the MD 200 may upgrade the warning to a more severe level (step 990) and the treatment being delivered may be modified, and/or an additional treatment may be provided (step 995). In an alternative embodiment, the step of upgrading the warning may be initially omitted and the treatment may be modified first, as indicated by the dotted line connecting blocks 980 and 995 and 990*a*. The MD 200 may then continue to determine whether the state of the status epilepticus is substantially controlled (step 980).

Upon a determination that the extreme event/state is substantially controlled (step 980), the warning may be downgraded and/or canceled (step 985). Further, the treatment parameter(s) used for the administration of the automatic treatment may be reported/logged (step 985). The MD 200 may then continue to perform body data acquisition (step 914).

In one embodiment, upon providing a warning to the patient, caregiver, and/or to a healthcare provider (step 910), the MD 200 may provide for the healthcare provider, the caregiver, and/or the patient to assume care/treatment responsibilities (step 962). Based upon one or more inputs received by the MD 200, a determination may be made as to whether to override the automated treatment (step 964). If it is determined that the automated treatment is not to be overridden, then the state of the automatic treatment is maintained (step 966).

If a determination is made that the automated treatment is to be overridden, a non-automated treatment plan is determined and executed (step 967). A more detailed description of the determining and executing a non-automated treatment plan is provided in FIG. 10 and accompanying description below. In one embodiment, upon determining and executing a non-automated treatment plan, this treatment plan may be set as the next automatic treatment that is executed by the MD 200 (step 968). The MD 200 then continues to perform body data acquisition (step 914). In an alternative embodiment, the step of setting the non-automatic treatment plan as the default automatic treatment plan may be omitted, as indicated by the dotted lines between blocks 967, 968 and 969.

Figure 10:
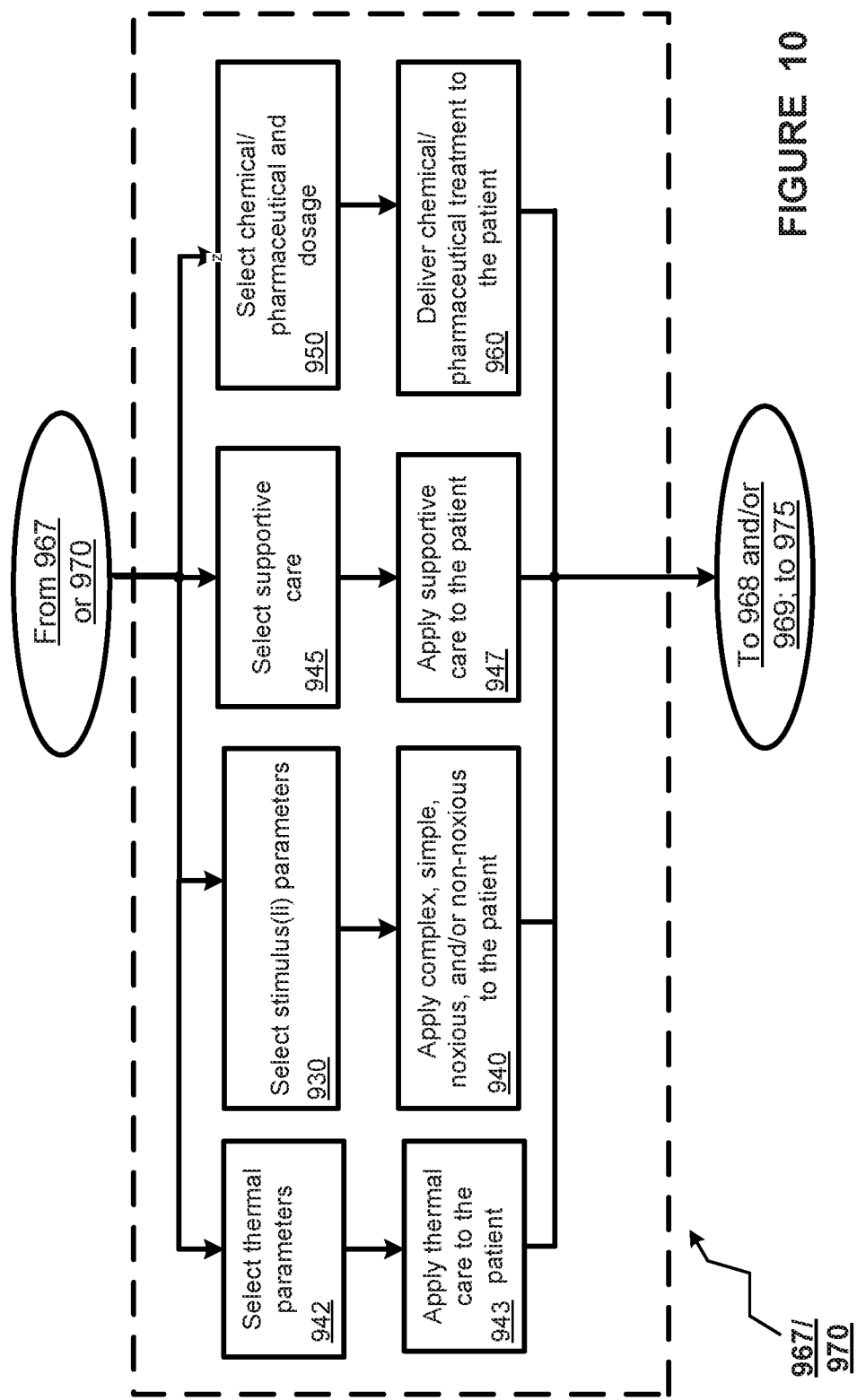
FIG. 10 illustrates a stylized diagram of determining and executing a treatment plan by a healthcare provider, caregiver and/or patient subsequent to overriding automated treatment, in accordance with one illustrative embodiment of the present invention.

Turning now to FIG. 10, a stylized depiction of the step of determining an automatic or a non-automatic treatment plan of steps 967/970 of FIG. 9, in accordance with one illustrative embodiment, is provided. The MD 200 may select a chemical/drug the dosage and rate of delivery (step 950) and deliver the drug/chemical to the patient (step 960). In addition to, or alternatively to, the chemical treatment, the MD 200 may select parameters of an electrical signal to treat the patient (step 930) and apply the specified electrical signal to a neural structure (e.g., a branch of the vagus nerve), cardiac structure, respiratory structure, dermis, sub-dermis, vascular structure, musculo-skeletal structure and/or the like of the patient (step 940). Further, in addition, or alternatively, the MD 200 may select one or more thermal parameters to specifically treat the extreme event/state with a thermal therapy (heating and/or cooling) (step 942) and apply it (step 943). The flow may then proceed to steps 968/969 and/or step 975. Further, in addition, or alternatively, the MD 200 may select one or more supportive care steps to treat the patient (step 945) and apply the specified supportive care (step 947).

Figure 11:
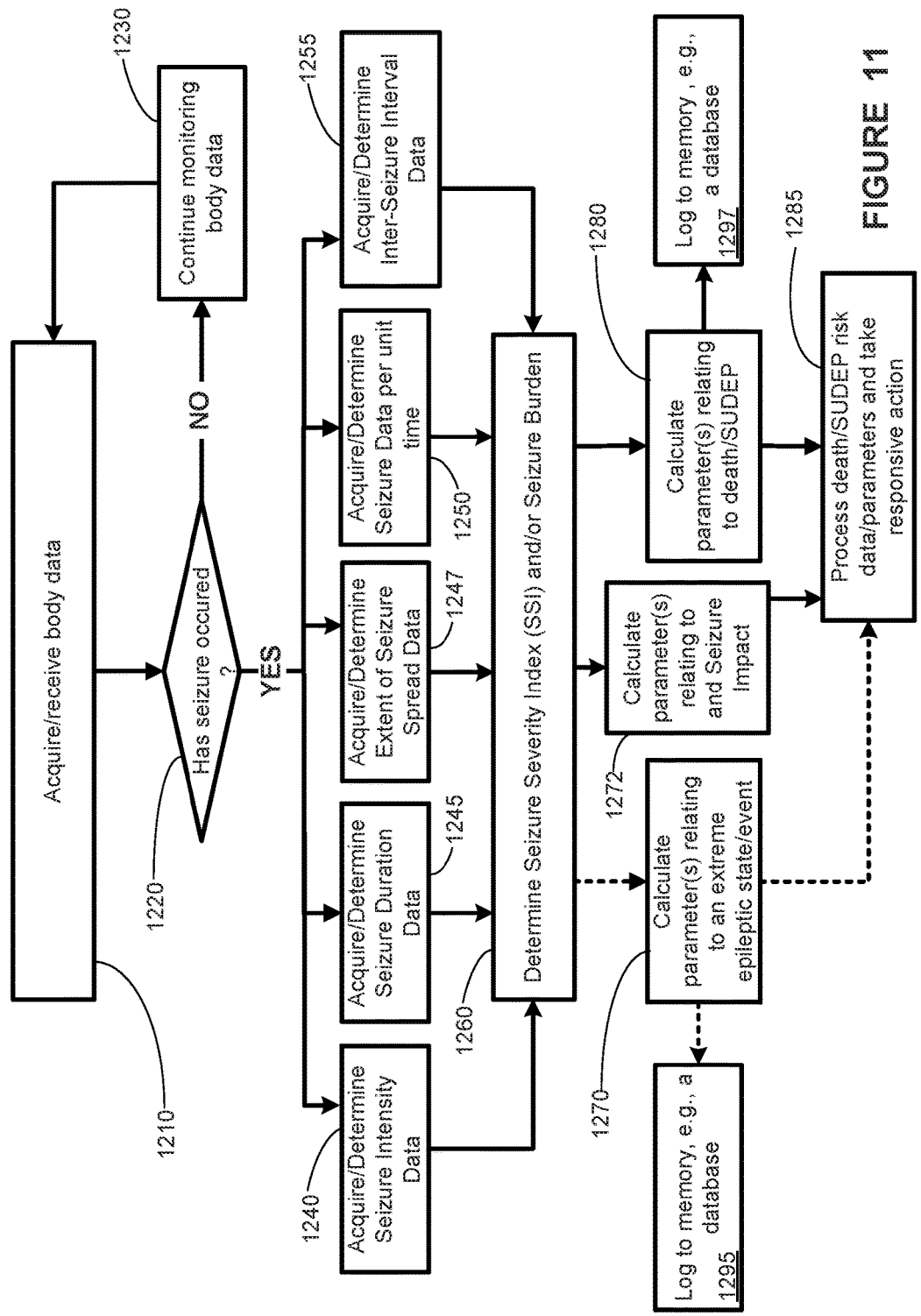
FIG. 11 provides a flowchart depiction of a method for identifying and/or managing an increased risk of death, in accordance with one illustrative embodiment of the present invention.

Turning now to FIG. 11, a flowchart depiction of a method for warning and/or taking action in response to determining a risk of death and/or SUDEP is provided, in accordance with one illustrative embodiment of the present invention. The medical device 200 acquires and/or receives body data at (step 1210). Typically, the body data collection unit 275 receives the body data. The body data may be indicative of whether or not a seizure or seizure event has occurred or is occurring. After performing buffering, amplification and A/D conversion of the body data, the medical device 200 determines if a seizure has occurred or is occurring (step 1220). Typically the seizure determination module 299 makes this determination based upon one or more calculations. If the medical device 200 determines that no seizure or seizure event has occurred, the medical device 200 will continue to monitor for body data (step 1230 and return the flow to step 1210).

If the medical device determines (at step 1220) that a seizure has occurred or is occurring, the method proceeds to acquire seizure intensity data (step 1240), seizure duration data (step 1245), extent of seizure data (step 1247), time spent in seizure data (step 1250) and/or inter-seizure interval data (step 1250). In one embodiment, one or more of an autonomic index, a neurologic index, a tissue stress index, a metabolic index or an endocrine index are acquired and/or determined using an SSI unit 295 (typically comprising an autonomic index unit 520, a neurologic index unit 510, a tissue stress marker index unit 550, an endocrine index unit 540 and a metabolic index unit 542). Steps 1240, 1245, 1250 and/or 1255 may begin at the same time and end at the same time (or at different times and in different combinations) according to different embodiments contemplated herein. In other words, steps 1240, 1245, 1250 and/or 1255 may begin and be completed substantially in parallel (i.e., at approximately the same time or at the same time) or independently of each other. The medical device determines an SSI value using the seizure intensity data, seizure duration data, time spent in seizure data and/or inter-seizure interval data (step 1260). Typically, the SSI value is determined by SSI unit 295. In one or more embodiments, additional data may also be used to determine the SSI value.

The determination of an SSI value(s) at step 1260 may, in some embodiments, be performed using one or more of a clustering analysis, a graphical analysis as a function of time with respect to a threshold(s) or a statistical analysis (e.g., a histogram) with respect to a number of standard deviations away from an actual or realized "normal" distribution. A clustering analysis may include determining changes in seizure clusters with respect to themselves and/or each other. Clusters may be grouped according to seizure event intensity and duration. For example, in one illustrative embodiment, a patient may have a first cluster of seizure events with relatively short duration and relatively low intensity and a second, smaller cluster with seizure events having relatively long duration and relatively high intensity. If either seizure event cluster increases in average duration and/or average intensity, this may indicate an increased risk of death and/or SUDEP. Similarly, if a cluster shifts outward, away from the origin (on a plot of duration versus intensity) causing the distance (graphically) between the two clusters to increase, such a shift/increase may represent an increased risk of death and/or SUDEP. If the average intensity and/or average duration of a cluster increases (e.g., the cluster includes an increasing number of seizure events with higher intensity and/or higher duration), this may also represent an increased risk of death and/or SUDEP.

In an alternate embodiment, the SSI value(s) may be determined by normalizing a seizure intensity value, a seizure duration value and/or a seizure spread value to obtain respective percentage values. The percentage values may be averaged to determine an SSI.

In other embodiments, the SSI may be determined based upon the duration of the seizure event and the peak intensity of the seizure event. In some such embodiments, the SSI may be calculated as the product of the peak intensity of the seizure event and the duration of the seizure event. The peak intensity may be the maximum value of any one, or any number, of body data values during a seizure event. For example, in one illustrative embodiment, a patient's heart rate (HR) may increase above a pre-determined threshold of 85 beats per minute during a seizure event. During the seizure event, the patient's HR may reach a maximum value of 135 beats per minute. For a seizure event lasting 30 seconds, the peak intensity of the seizure event (i.e., 135) may be multiplied by the duration (i.e., 30) to obtain an SSI value. In this example, an SSI above a pre-determined (or dynamic) value may indicate a risk of death and/or SUDEP. Similarly, an SSI value above or below a pre-determined (or dynamic) percentile based upon historical patient data may indicate a risk of death and/or SUDEP. For example, if a given SSI value for a patient is above the ninetieth percentile (or below the tenth percentile) of the patient's past SSI values, the patient may be at an increase risk of death and/or SUDEP.

The medical device 200 may calculate one or more parameters related to death and/or SUDEP (step 1280). The calculation of SUDEP parameter(s) may be performed by a Death/SUDEP risk determination unit 285. The calculation of death/SUDEP parameter(s) may include a calculation using one or more SSI values. Upon calculating death/SUDEP parameter(s), the MD 200 may log the parameters to a memory (e.g., a database) (step 1297). The death/SUDEP parameter(s) may be stored in an external memory (e.g., the database unit 250 and/or the local database unit 255), and/or in memory that is internal to the MD 200 (e.g., memory 217). The death/SUDEP parameters may also be sent to an external device 265.

Figure 12:
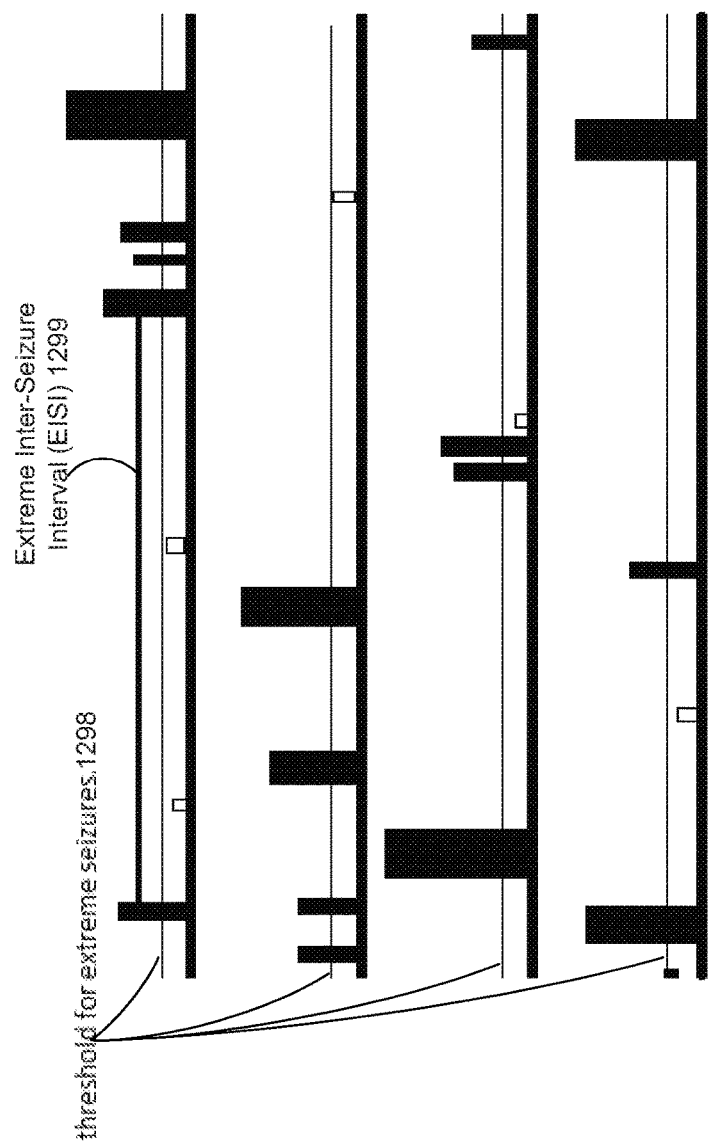
FIG. 12 depicts a stylized graphical representation of a seizure time series, in accordance with one or more embodiments.

Turning now to FIG. 12, a stylized graphical representation of a seizure time series, in accordance with one or more embodiments, is depicted. Figure X depicts a seizure time series containing a log of extreme (filled rectangles) and non-extreme seizures (open rectangles) over a 4 week period (each level corresponds to 1 week) as it would be collected in accordance with one embodiment. Extreme seizures in FIG. 12 may be defined by their intensity (height of rectangle) and/or duration (width of rectangle). An extreme seizure, for example, may be a seizure that crosses a threshold for extreme seizures 1298 and/or a seizure with an extreme inter-seizure interval (EISI) 1299. A non-extreme seizure may not cross the threshold for extreme seizures 1298. Using this log, the following may be computed: 1. Time spent in seizure (TSS) which is the sum of time spent in extreme ($TSS_E$) and non-extreme seizure ($TSS_{Ne}$) over a given time period (e.g., 1 month); 2. Cumulative seizure severity index (cSSI) calculated using at least one of intensity, duration and/or extent of spread; 3. Inter-seizure interval (ISI) which may be segregated into extreme inter-seizure interval ($ISI_E$) and/or non-extreme ($ISI_{nE}$). In one embodiment, these statistics may be used to compute a monthly seizure burden (SB) either total (extreme and non-extreme) or only extreme: SB=TSS×cSSI. In one embodiment, these statistics may be used to compute a monthly seizure density (SD) either total or only extreme. Seizure density may be defined as a) SD=TSS×cSSI/Time (in elapsed time between the end of the first and last seizures in a given time window multiplied by seizure frequency) and/or b) SD=(mean SSI× TSS×seizure frequency)/(maximum ISI×minimum ISI). In one embodiment, a window length over which the observations were made may be added to the denominator in order to determine a scalable SD. Other mathematical representations such as mean SSI, mean ISI and/or the like may also be used. While FIG. 12 is described in terms of a 4 week or monthly time period, it is noted that any other meaningful time period may be used.

Figure 13:
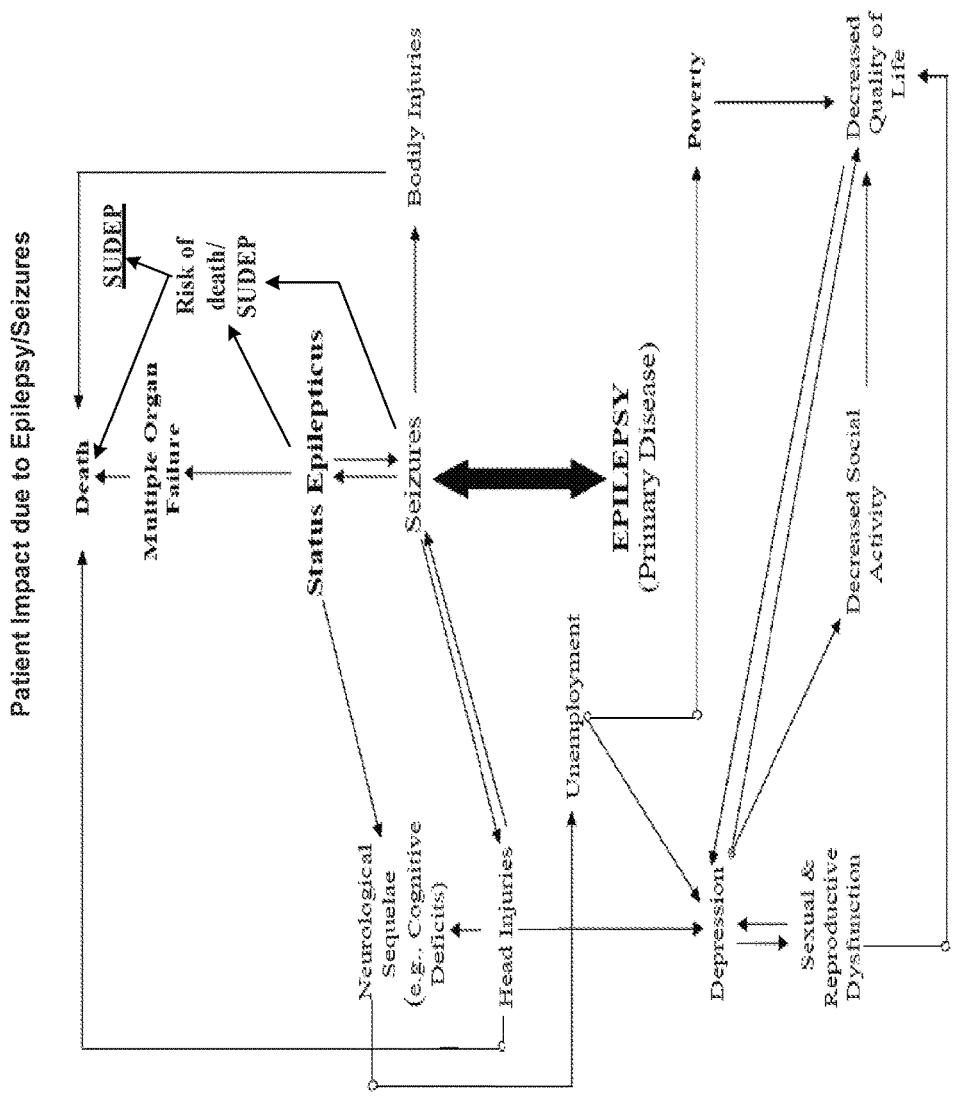
FIG. 13 depicts a stylized graphical representation of relationships between epilepsy and some of its comorbidities, with the directionality of each arrow indicating an amplifying effect, in accordance with one or more embodiments.

Turning to FIG. 13, a stylized graphical representation of relationships between epilepsy and some of its comorbidities, with the directionality of each arrow indicating an amplifying effect, is depicted in accordance with one or more embodiments. Pharmaco-resistant seizures are associated with an, eventual impairment of cognitive functions and mental health, and markedly degraded quality of life for patients and their families. Seizures may impair motor control, responsiveness to a wide class of stimuli, and other cognitive functions. Certain pharmacological agents used for treatment of epilepsy cause osteoporosis, reproductive dysfunction, liver and bone marrow damage, and in rare cases, death. As exemplified in FIG. 13, seizures, the main manifestation of epilepsy, can lead to bodily/head injuries and in extreme cases to organ failure, each of which increases risk of death. Head injuries may lead to other physical problems that may present or increase a risk of death and/or SUDEP in a patient. Seizures, their co-morbidities, and injuries may also lead to other problems, such as depression (and increased risk of suicide), sexual/reproductive dysfunction, decreased social activity and poor quality of life. In one embodiment of this inventions (as described in A Systems Approach to Disease State and Health Assessment by Dr. Ivan Osorio (U.S. application Ser. No. 12/816,357), incorporated herein in its entirety) quality of life (QOL) may be assessed at regular intervals to determine among others, risk of suicide and institute appropriate interventions (e.g., psychiatric) or when the circumstances dictate it (e.g., patient suffered a brain injury during a fall caused by a seizure).

The methods and apparatuses disclosed and claimed herein may be made and executed without undue experimentation in light of the present disclosure. While the methods and apparatus of embodiments of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve, and/or to other body systems related to those discussed herein to achieve particular results in treating patients having epilepsy, depression, or other medical conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

The invention claimed is:

1. A method for monitoring an increased risk of death relating to a patient with epilepsy, comprising:
receiving cardiac data into a medical device;
determining via the medical device at least one cardiac index based upon the cardiac data;
determining via the medical device the increased risk of death associated with epilepsy based on the at least one cardiac index being in an extreme state;
initiating at least one of issuing a warning of an occurrence of the increased risk of death and delivering a therapy based on the occurrence of the increased risk of death; and
logging information related to the increased risk of death.

2. The method of claim 1, wherein the extreme state relates to a respiratory dysfunction.

3. The method of claim 1, further comprising at least one of determining an autonomic index, classifying the autonomic index, ranking the autonomic index, reporting the autonomic index, and logging the autonomic index.

4. The method of claim 1, further comprising at least one of reporting and logging at least one autonomic index over a first predetermined time period before the increased risk of death is determined.

5. The method of claim 1, further comprising determining that an increased risk of death state has returned to a baseline value.

6. The method of claim 1, further comprising determining an autonomic index where the autonomic index includes at least one of a respiratory rate, a respiratory rhythm, a respiratory pattern, a cardiac rate, and a cardiac rhythm over a time period related to the increased risk of death.

7. A medical device configured to monitor for an increased risk of death to a patient with epilepsy, comprising:
one or more processors configured to receive cardiac data from one or more sensors, the one or more processors configured to determining a cardiac index based on the cardiac data, the one or more processors configured to determining the increased risk of death associated with epilepsy based on the cardiac index, the one or more processors configured to determine one or more grades associated with the determined increased risk of death, and the one or more processors configured to issue one or more warnings based on the one or more grades determinations.

8. The medical device of claim 7, wherein the one or more processors are configured to issue a first warning based on a first grade determination.

9. The medical device of claim 8, wherein the one or more processors are configured to issue a second warning based on a second grade determination.

10. The medical device of claim 7, wherein the one or more processors are configured to issue no warning based on a first grade determination and a first characteristic for a first patient determined via the one or more processors.

11. The medical device of claim 10, wherein the one or more processors are configured to issue a first warning based on the first grade determination and the first characteristic for a second patient determined via the one or more processors.

12. The medical device of claim 11, wherein the one or more processors are configured to issue a second warning based on the first grade determination and the first characteristic for a third patient determined via the one or more processors.

13. The medical device of claim 7, wherein the one or more processors are configured to issue an extreme warning based on an Nth grade determination.

14. The medical device of claim 7, wherein the one or more processors are configured to initiate an action based on at least one of a surrounding determination and a grade determination.

15. The medical device of claim 14, wherein the action is at least one of turning on a device and turning off the device.

16. A method of monitoring for an increased risk of death to a patient with epilepsy, comprising:
receiving cardiac data from one or more sensors;
determining via one or more processors a cardiac index based on the cardiac data;
determining the increased risk of death associated with epilepsy based on the cardiac index;
determining one or more grades associated with the determined increased risk of death, and issuing one or more warnings based on the one or more grades determinations.

17. The method of claim 16, further comprising issuing a first warning and delivering a first therapy based on a first grade determination.

18. The method of claim 17, further comprising issuing a second warning and delivering a second therapy based on a second grade determination.

19. The method of claim 16, further comprising issuing no warning and not delivering a therapy based on a first grade determination and a first characteristic for a first patient determined via the one or more processors.

20. The method of claim 19, further comprising issuing a first warning and delivering a first therapy based on the first grade determination and the first characteristic for a second patient determined via the one or more processors.

21. The method of claim 20, further comprising issuing a second warning and delivering a second therapy based on the first grade determination and the first characteristic for a third patient determined via the one or more processors.

22. The method of claim 16, further comprising issuing an extreme warning and delivering a therapy based on an Nth grade determination.

23. The method of claim 16, further comprising initiating an action based on at least one of a surrounding determination and a grade determination.

24. The method of claim 23, wherein the action is at least one of turning on a device and turning off the device.

* * * * *